US012668621B2

(12) United States Patent
Freund et al.

(10) Patent No.: US 12,668,621 B2
(45) Date of Patent: Jun. 30, 2026

(54) COMPOSITIONS AND METHODS FOR THE TREATMENT OF TUBERCULOSIS

(71) Applicant: Ramot at Tel-Aviv University Ltd., Tel-Aviv (IL)

(72) Inventors: Natalia Freund, Tel-Aviv (IL); Ronen Weiss, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1205 days.

(21) Appl. No.: 17/627,167

(22) PCT Filed: Jul. 16, 2019

(86) PCT No.: PCT/IL2019/050801
§ 371 (c)(1),
(2) Date: Jan. 14, 2022

(87) PCT Pub. No.: WO2021/009740
PCT Pub. Date: Jan. 21, 2021

(65) Prior Publication Data
US 2022/0281960 A1 Sep. 8, 2022

(51) Int. Cl.
| | |
|---|---|
| *A61P 31/06* | (2006.01) |
| *C07K 16/1289* | (2026.01) |
| *C12N 1/20* | (2026.01) |
| *C12N 15/70* | (2006.01) |
| *C12P 21/00* | (2006.01) |
| *G01N 33/569* | (2006.01) |

(52) U.S. Cl.
CPC .......... *C07K 16/1289* (2013.01); *A61P 31/06* (2018.01); *C12N 1/20* (2013.01); *C12N 15/70* (2013.01); *C12P 21/005* (2013.01); *G01N 33/5695* (2013.01); *C07K 2317/21* (2013.01); *C12N 2800/101* (2013.01)

(58) Field of Classification Search
CPC . A61P 31/06; C12N 1/20; C12N 15/70; C12P 21/005; G01N 33/5695
See application file for complete search history.

(56) References Cited

U.S. PATENT DOCUMENTS

| | | | |
|---|---|---|---|
| 2008/0171345 A1 * | 7/2008 | Belisle .............. | G01N 33/5695 530/350 |
| 2017/0023586 A1 | 1/2017 | Felgner et al. | |

FOREIGN PATENT DOCUMENTS

| | | |
|---|---|---|
| CN | 107970444 | 5/2018 |
| WO | WO 2021/009740 | 1/2021 |
| WO | WO 2021/009740 A8 | 3/2021 |

OTHER PUBLICATIONS

MacCallum et al (Antibody-antigen Interactions: Contact Analysis and Binding Site Topography, J. Mol. Biol. (1996) 262, 732-745) (Year: 1996).*
Holm et al (Functional mapping and single chain construction of the anti-cytokeratin 8 monoclonal antibody TS1, Molecular Immunology 44 (2007) 1075-1084) (Year: 2007).*
Casset et al (A peptide mimetic of an anti-CD4 monoclonal antibody by rational design, Biochemical and Biophysical Research Communications 307 (2003) 198-205) (Year: 2003).*
Chen et al (Selection and Analysis of an Optimized Anti-VEGF Antibody: Crystal Structure of an Affinity-matured Fab in Complex with Antigen, J. Mol. Biol. (1999) 293, 865±881) (Year: 1999).*
Rudikoff et al (Single amino acid substitution altering antigen-binding specificity, Proc. Nat. Acad. Sci. USA, vol. 79, pp. 1979-1983, Mar. 1982) (Year: 1982).*
International Search Report and the Written Opinion Dated Oct. 10, 2019 From the International Searching Authority Re. Application No. PCT/IL2019/050801. (14 Pages).
Freund et al. "A New Glycan-Dependent CD4-Binding Site Neutralizing Antibody Exerts Pressure on HIV-1 In Vivo", PLOS Pathogens, 11(10): e1005238-1-e1005238-19, Oct. 30, 2015.
Freund et al. "Amplification of Highly Mutated Human Ig Lamda Light Chains From An HIV-1 Infected Patient", Journal of Immunological Methods, 418: 61-65, Published Online Feb. 7, 2015.
Freund et al. "Coexistence of Potent HIV-1 Broadly Neutralizing Antibodies and Antibody-Sensitive Viruses in A Viremic Controller", Science Translational Medicine, 9(373): eaa12140-1-eaal2140-13, Jan. 18, 2017.
Furuya et al. "Increased Susceptibility of IgA-Deficient Mice to Pulmonary Francisella Tularensis Live Vaccine Strain Infection", Infection and Immunity, 81(9): 3434-3441, Published Online Jul. 8, 2013.
Rodriguez et al. "Role of IgA in the Defense Against Respiratory Infections IgA Deficient Mice Exhibited Increased Susceptibility to Intranasal Infection With *Mycobacterium bovis* BCG", Vaccine, 23(20): 2565-2572, Available Online Dec. 9, 2004.
Shin et al. "*Mycobacterium tuberculosis* HBHA Protein Reacts Strongly With the Serum Immunoglobulin M of Tuberculosis Patients", Clinical and Vaccine Immunology, 13(8): 869-875, Aug. 2006.
Weiss et al. "Anti-*Mycobacterium tuberculosis* Antibodies Isolated From An Infected Donor", Tel Aviv University, Israel, Poster, Jan. 17, 2019.
Invitation Pursuant to Rule 62a(1) EPC and Rule 63(1) EPC Dated Jan. 3, 2023 From the European Patent Office Re. Application No. 19937582.5. (5 Pages).
Supplementary Partial European Search Report and the European Search Opinion Dated Mar. 13, 2023 From the European Patent Office Re. Application No. 19937582.5. (14 Pages).
Watson et al. "Human Antibodies Targeting a *Mycobacterium* Transporter Protein Mediate Protection Against Tuberculosis", Nature Communications 12(1): Article No. 602, 1-11, Jan. 27, 2021.

* cited by examiner

*Primary Examiner* — Nelson B Moseley, II
*Assistant Examiner* — Dennis J Sullivan

(57) ABSTRACT

A human antibody comprising an antigen binding domain which binds PstS1 of *Mycobacterium tuberculosis* (TB) for use in preventing or treating TB infection in a subject in need thereof is provided. Also provided are vaccine compositions and conjugates of such antibodies.

1 Claim, 4 Drawing Sheets

Specification includes a Sequence Listing.

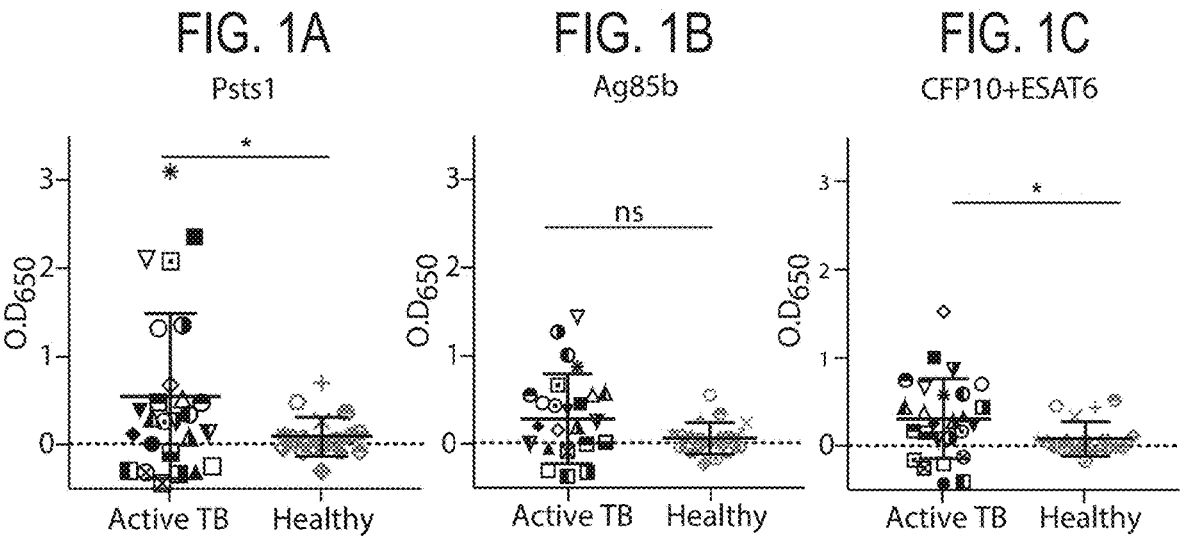
FIG. 1A
Psts1
FIG. 1B
Ag85b
FIG. 1C
CFP10+ESAT6
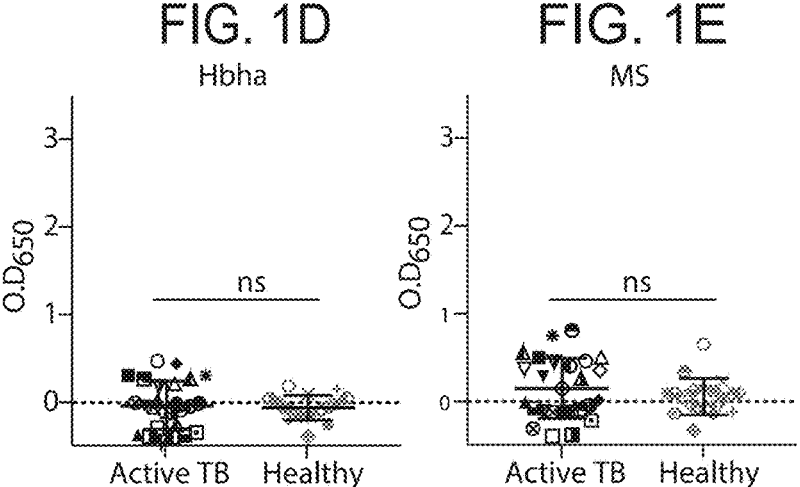
FIG. 1D
Hbha
FIG. 1E
MS
FIG. 1F
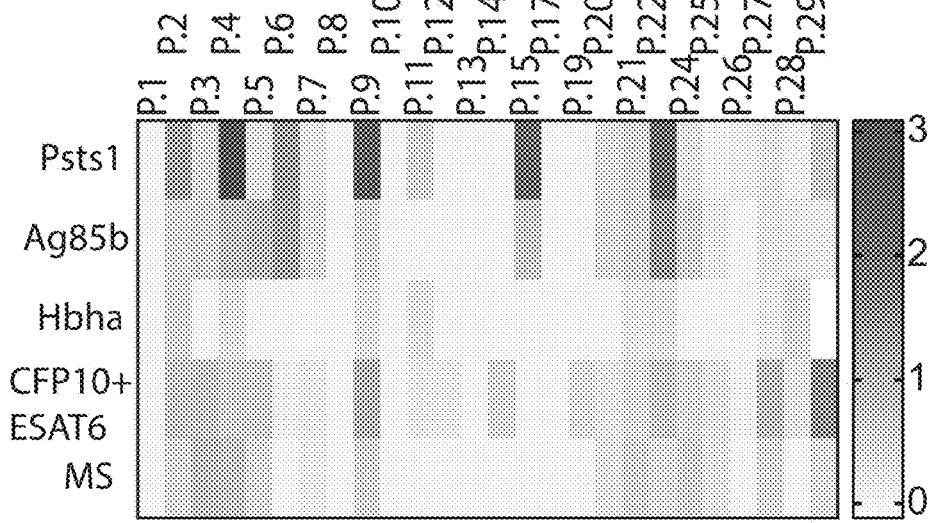

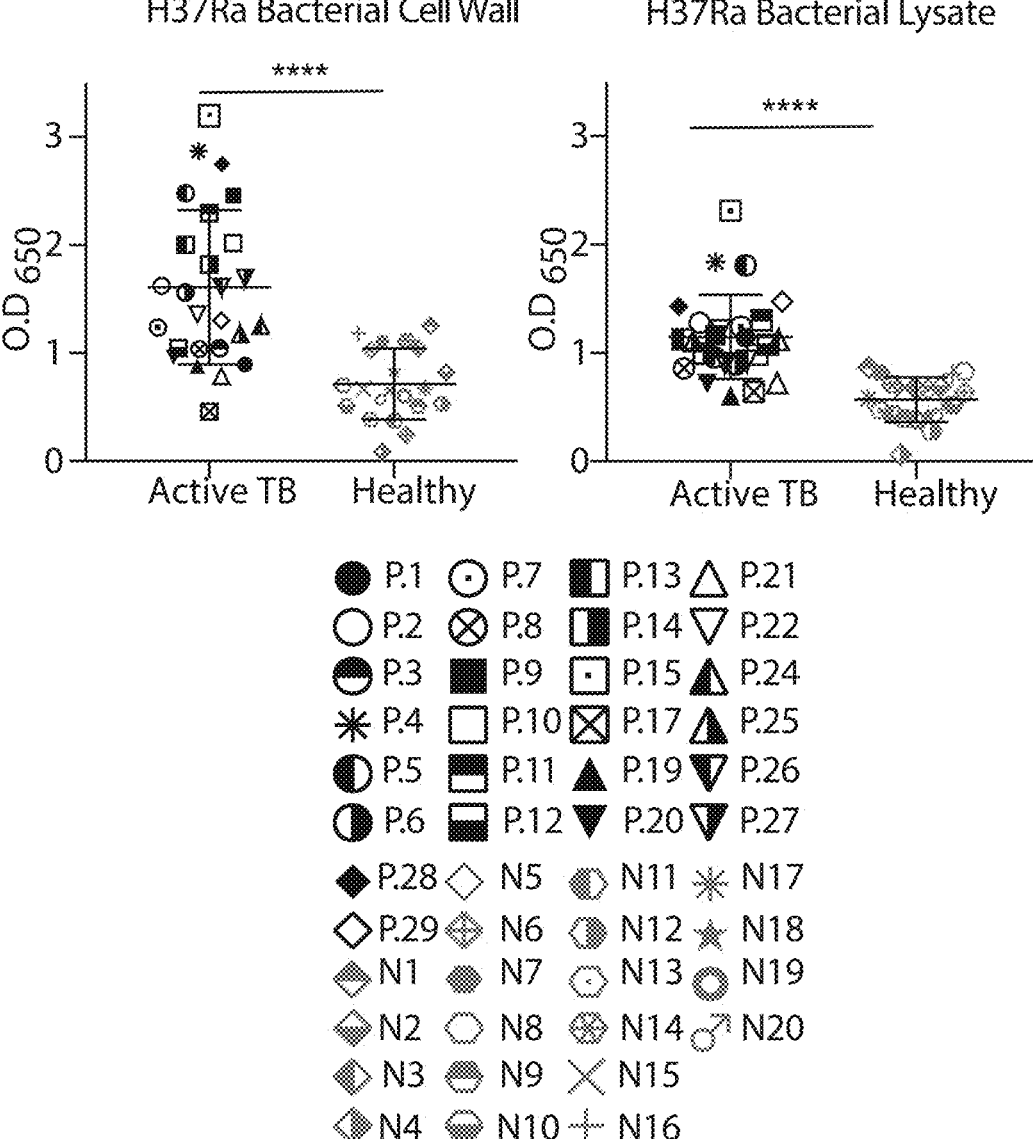

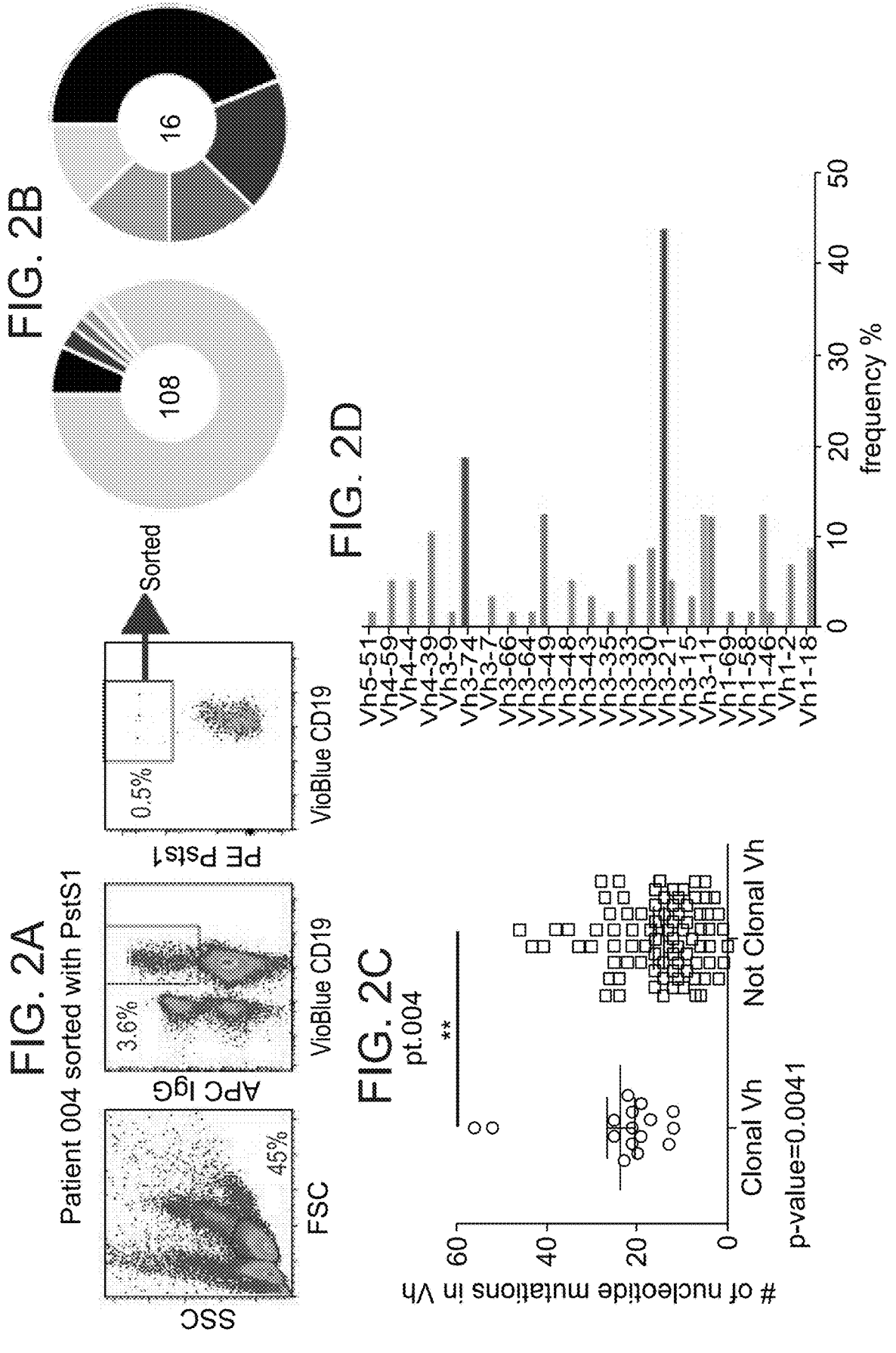

FIG. 3A
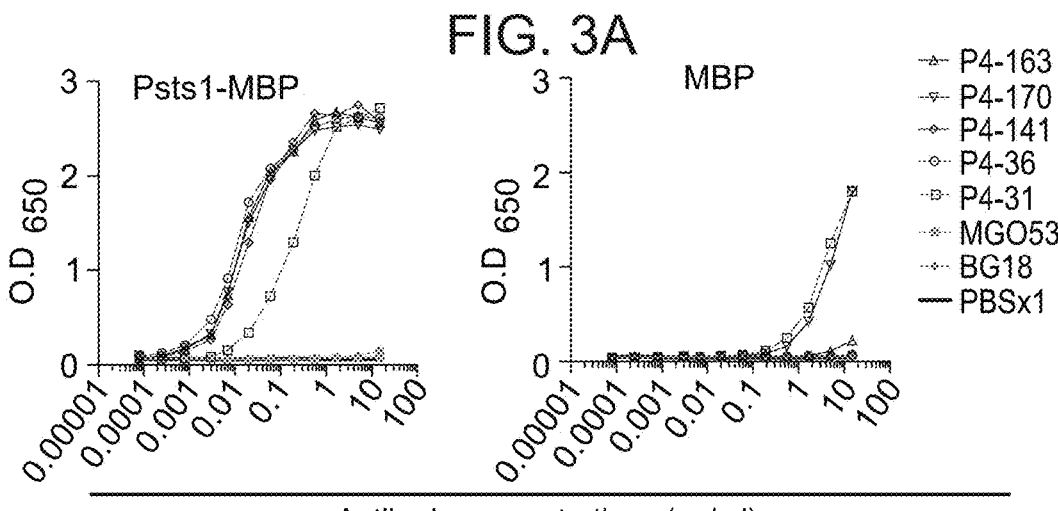
FIG. 3B          FIG. 3C
FIG. 4
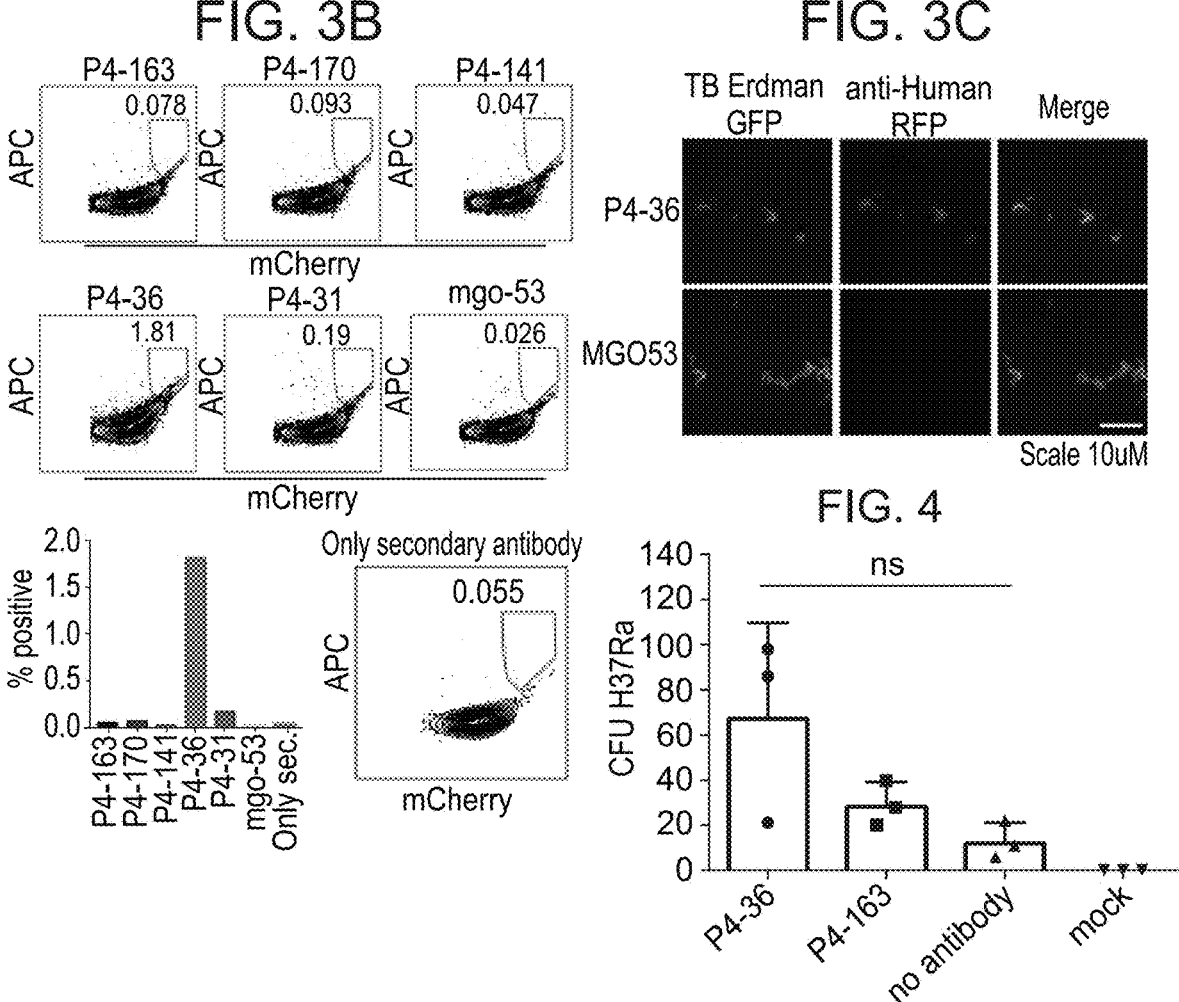

SEQUENCE LISTING

<160> NUMBER OF SEQ ID NOS: 131

<210> SEQ ID NO 1
<211> LENGTH: 125
<212> TYPE: PRT
<213> ORGANISM: Artificial sequence
<220> FEATURE:
<223> OTHER INFORMATION: P4-110 IgH amino acid sequence -continued

<400> SEQUENCE: 1

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Arg His
            20                  25                  30

Thr Met His Trp Val Arg Leu Ala Pro Gly Lys Gly Leu Glu Trp Val
        35                  40                  45

Ser Ser Ile Leu Ser Ser Pro Thr Tyr Ile Tyr Tyr Ala Asp Ser Val
    50                  55                  60

Lys Gly Arg Phe Thr Ile Ser Arg Asp Asn Ser Gly Asn Ser Leu Phe
65                  70                  75                  80

Leu Gln Met Asn Ser Leu Arg Val Asp Asp Thr Ala Val Tyr Tyr Cys
                85                  90                  95

Ala Arg Gly Asp Tyr Tyr Tyr Asp Gly Val Ala Ser Asp Pro His Phe
            100                 105                 110

Asp Asn Trp Gly Gln Gly Thr Leu Val Thr Val Ser Ser
        115                 120                 125

<210> SEQ ID NO 2
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 2

Gly Phe Thr Phe Ser Arg His Thr
1               5

<210> SEQ ID NO 3
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 3

Ile Leu Ser Ser Pro Thr Tyr Ile
1               5

<210> SEQ ID NO 4
<211> LENGTH: 18
<212> TYPE: PRT
<213> ORGANISM: Artificial sequence
<220> FEATURE:
<223> OTHER INFORMATION: complementarity determining region (CDR) amino
      acid sequence

<400> SEQUENCE: 4

Ala Arg Gly Asp Tyr Tyr Tyr Asp Gly Val Ala Ser Asp Pro His Phe
1               5                   10                  15

Asp Asn

<210> SEQ ID NO 5
<211> LENGTH: 110
<212> TYPE: PRT
<213> ORGANISM: Artificial sequence
<220> FEATURE:
<223> OTHER INFORMATION: P4-110 IgL amino acid sequence

<400> SEQUENCE: 5

```
Gln Ser Val Leu Thr Gln Thr Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Tyr Val Tyr Trp Phe Gln Gln Phe Pro Gly Ala Ala Pro Gln Leu Leu
        35                  40                  45

Ile Ser Arg Asn Ile Gln Arg Pro Ser Gly Val Pro Ala Arg Phe Ser
    50                  55                  60

Gly Ser Lys Ser Asp Thr Ser Ala Ser Leu Ala Ile Ser Gly Leu Arg
65                  70                  75                  80

Ser Glu Asp Glu Ala His Tyr Tyr Cys Ala Ala Trp Asp Asp Ser Leu
                85                  90                  95

Ser Gly Val Val Phe Gly Gly Gly Thr Lys Val Thr Val Leu
            100                 105                 110
```

<210> SEQ ID NO 6
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 6

```
Arg Ser Asn Ile Gly Ser Asn Tyr
1               5
```

<210> SEQ ID NO 7
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 7

```
Arg Asn Ile
1
```

<210> SEQ ID NO 8
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 8

```
Ala Ala Trp Asp Asp Ser Leu Ser Gly Val Val
1               5                   10
```

<210> SEQ ID NO 9
<211> LENGTH: 125
<212> TYPE: PRT
<213> ORGANISM: Artificial sequence
<220> FEATURE:
<223> OTHER INFORMATION: P4-143 IgH amino acid sequence

<400> SEQUENCE: 9

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Glu Ser His
```

-continued

```
                20              25              30

Arg Met His Trp Val Arg Gln Ala Pro Gly Lys Gly Leu Glu Trp Val
         35              40              45

Ser Ser Ile Ile Ser Ser Arg Thr Tyr Ile Tyr Tyr Ala Asp Ser Val
     50              55              60

Lys Gly Arg Phe Thr Ile Ser Arg Asp Asn Ser Arg Asn Ser Leu Phe
65              70              75              80

Leu Gln Met Asn Ser Leu Arg Ala Glu Asp Thr Ala Val Tyr Tyr Cys
             85              90              95

Ala Arg Gly Asp Tyr Tyr Tyr Asp Gly Val Ala Ser Asp Pro His Phe
             100             105             110

Asp Asn Trp Gly Gln Gly Thr Leu Val Thr Val Ser Ser
         115             120             125
```

```
<210> SEQ ID NO 10
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 10

Gly Phe Thr Phe Glu Ser His Arg
1               5
```

```
<210> SEQ ID NO 11
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 11

Ile Ile Ser Ser Arg Thr Tyr Ile
1               5
```

```
<210> SEQ ID NO 12
<211> LENGTH: 18
<212> TYPE: PRT
<213> ORGANISM: Artificial sequence
<220> FEATURE:
<223> OTHER INFORMATION: complementarity determining region (CDR) amino
      acid sequence

<400> SEQUENCE: 12

Ala Arg Gly Asp Tyr Tyr Tyr Asp Gly Val Ala Ser Asp Pro His Phe
1               5               10              15

Asp Asn
```

```
<210> SEQ ID NO 13
<211> LENGTH: 80
<212> TYPE: PRT
<213> ORGANISM: Artificial sequence
<220> FEATURE:
<223> OTHER INFORMATION: P4-143 IgL amino acid sequence

<400> SEQUENCE: 13

Ser Asn Tyr Val Tyr Trp Phe Gln Gln Leu Pro Gly Thr Ala Pro Gln
1               5               10              15

Leu Leu Ile Tyr Arg Asn Ile Gln Arg Pro Ser Gly Val Pro Ala Arg
             20              25              30
```

-continued

```
Phe Ser Gly Ser Lys Ser Gly Thr Ser Ala Ser Leu Ala Ile Ser Gly
        35                  40                  45

Leu Arg Ser Glu Asp Glu Ala Asp Tyr Tyr Cys Ala Thr Trp Asp Asp
    50                  55                  60

Ser Leu Ser Gly Val Val Phe Gly Gly Gly Thr Lys Val Thr Val Leu
65                  70                  75                  80

<210> SEQ ID NO 14
<211> LENGTH: 7
<212> TYPE: PRT
<213> ORGANISM: Artificial sequence
<220> FEATURE:
<223> OTHER INFORMATION: complementarity determining region (CDR) amino
      acid sequence

<400> SEQUENCE: 14

Ser Asn Ile Gly Ser Asn Tyr
1               5

<210> SEQ ID NO 15
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 15

Arg Asn Ile
1

<210> SEQ ID NO 16
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 16

Ala Thr Trp Asp Asp Ser Leu Ser Gly Val Val
1               5                   10

<210> SEQ ID NO 17
<211> LENGTH: 125
<212> TYPE: PRT
<213> ORGANISM: Artificial sequence
<220> FEATURE:
<223> OTHER INFORMATION: P4-163 IgH amino acid sequence

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Glu Ser His
            20                  25                  30

Arg Met His Trp Val Arg Gln Ala Pro Gly Lys Gly Leu Glu Trp Val
        35                  40                  45

Ser Ser Ile Ile Ser Ser Arg Thr Tyr Ile Tyr Tyr Ala Asp Ser Val
    50                  55                  60

Lys Gly Arg Phe Thr Ile Ser Arg Asp Asn Ser Arg Asn Ser Leu Phe
65                  70                  75                  80

Leu Gln Met Asn Ser Leu Arg Ala Glu Asp Thr Ala Val Tyr Tyr Cys
                85                  90                  95
```

```
Ala Arg Gly Asp Tyr Tyr Tyr Asp Gly Val Ala Ser Asp Pro His Phe
            100                 105                 110

Asp Asn Trp Gly Gln Gly Thr Leu Val Thr Val Ser Ser
        115                 120                 125

<210> SEQ ID NO 18
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 18

Gly Phe Thr Phe Glu Ser His Arg
1               5

<210> SEQ ID NO 19
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 19

Ile Ile Ser Ser Arg Thr Tyr Ile
1               5

<210> SEQ ID NO 20
<211> LENGTH: 18
<212> TYPE: PRT
<213> ORGANISM: Artificial sequence
<220> FEATURE:
<223> OTHER INFORMATION: complementarity determining region (CDR) amino
      acid sequence

<400> SEQUENCE: 20

Ala Arg Gly Asp Tyr Tyr Tyr Asp Gly Val Ala Ser Asp Pro His Phe
1               5                  10                  15

Asp Asn

<210> SEQ ID NO 21
<211> LENGTH: 110
<212> TYPE: PRT
<213> ORGANISM: Artificial sequence
<220> FEATURE:
<223> OTHER INFORMATION: P4-163 IgL amino acid sequence

<400> SEQUENCE: 21

Gln Ser Val Leu Thr Gln Pro Pro Ser Ala Ser Gly Thr Pro Gly Gln
1               5                  10                  15

Arg Val Thr Ile Ser Cys Ser Gly Gly Arg Ser Asn Ile Gly Ser Asn
            20                  25                  30

Tyr Val Tyr Trp Phe Gln Gln Leu Pro Gly Thr Ala Pro Gln Leu Leu
        35                  40                  45

Ile Tyr Arg Asn Ile Gln Arg Pro Ser Gly Val Pro Ala Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95
```

```
Ser Gly Val Val Phe Gly Gly Gly Thr Lys Val Thr Val Leu
            100                 105                 110

<210> SEQ ID NO 22
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 22

Arg Ser Asn Ile Gly Ser Asn Tyr
1               5

<210> SEQ ID NO 23
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 23

Arg Asn Ile
1

<210> SEQ ID NO 24
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 24

Ala Thr Trp Asp Asp Ser Leu Ser Gly Val Val
1               5                   10

<210> SEQ ID NO 25
<211> LENGTH: 125
<212> TYPE: PRT
<213> ORGANISM: Artificial sequence
<220> FEATURE:
<223> OTHER INFORMATION: P4-123 IgH amino acid sequence

<400> SEQUENCE: 25

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Glu Ser His
            20                  25                  30

Arg Met His Trp Val Arg Gln Ala Pro Gly Lys Gly Leu Glu Trp Val
        35                  40                  45

Ser Ser Ile Ile Ser Ser Arg Thr Tyr Ile Tyr Tyr Ala Asp Ser Val
    50                  55                  60

Lys Gly Arg Phe Thr Ile Ser Arg Asp Asn Ser Arg Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Tyr Asp Gly Val Ala Ser Asp Pro His Phe
            100                 105                 110

Asp Asn Trp Gly Gln Gly Thr Leu Val Thr Val Ser Ser
            115                 120                 125
```

```
<210> SEQ ID NO 26
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 26

Gly Phe Thr Phe Glu Ser His Arg
1               5

<210> SEQ ID NO 27
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 27

Ile Ile Ser Ser Arg Thr Tyr Ile
1               5

<210> SEQ ID NO 28
<211> LENGTH: 18
<212> TYPE: PRT
<213> ORGANISM: Artificial sequence
<220> FEATURE:
<223> OTHER INFORMATION: complementarity determining region (CDR) amino
      acid sequence

<400> SEQUENCE: 28

Ala Arg Gly Asp Tyr Tyr Tyr Asp Gly Val Ala Ser Asp Pro His Phe
1               5                   10                  15

Asp Asn

<210> SEQ ID NO 29
<211> LENGTH: 110
<212> TYPE: PRT
<213> ORGANISM: Artificial sequence
<220> FEATURE:
<223> OTHER INFORMATION: P4-123 IgL amino acid sequence

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Gly Arg Ser Asn Ile Gly Ser Asn
                20                  25                  30

Tyr Val Tyr Trp Phe Gln Gln Leu Pro Gly Thr Ala Pro Gln Leu Leu
            35                  40                  45

Ile Tyr Arg Asn Ile Gln Arg Pro Ser Gly Val Pro Ala Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Val Val Phe Gly Gly Gly Thr Lys Val Thr Val Leu
            100                 105                 110

<210> SEQ ID NO 30
<211> LENGTH: 8
<212> TYPE: PRT
```

```
<213> ORGANISM: Artificial sequence
<220> FEATURE:
<223> OTHER INFORMATION: complementarity determining region (CDR) amino
      acid sequence

<400> SEQUENCE: 30

Arg Ser Asn Ile Gly Ser Asn Tyr
1               5

<210> SEQ ID NO 31
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 31

Arg Asn Ile
1

<210> SEQ ID NO 32
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 32

Ala Thr Trp Asp Asp Ser Leu Ser Gly Val Val
1               5                   10

<210> SEQ ID NO 33
<211> LENGTH: 125
<212> TYPE: PRT
<213> ORGANISM: Artificial sequence
<220> FEATURE:
<223> OTHER INFORMATION: P4-170 IgH amino acid sequence

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Arg Met His Trp Val Arg Gln Ala Pro Gly Lys Gly Leu Glu Trp Val
        35                  40                  45

Ser Ser Ile Ile Ser Ser Arg Thr Tyr Ile Tyr Tyr Ala Asp Ser Val
    50                  55                  60

Lys Gly Arg Phe Thr Ile Ser Arg Asp Asn Ser Gly Asn Ser Leu Phe
65                  70                  75                  80

Leu Gln Met Asn Ser Leu Arg Val Glu Asp Thr Ala Val Tyr Tyr Cys
                85                  90                  95

Ala Arg Gly Asp Tyr Tyr Tyr Asp Gly Val Ala Ser Asp Pro His Phe
            100                 105                 110

Asp Asn Trp Gly Gln Gly Thr Leu Val Thr Val Ser Ser
        115                 120                 125

<210> SEQ ID NO 34
<211> LENGTH: 8
<212> TYPE: PRT
<213> ORGANISM: Artificial sequence
<220> FEATURE:
<223> OTHER INFORMATION: complementarity determining region (CDR) amino
``` acid sequence

<400> SEQUENCE: 34

Gly Phe Thr Phe Ser Ser His Arg
1               5

<210> SEQ ID NO 35
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 35

Ile Ile Ser Ser Arg Thr Tyr Ile
1               5

<210> SEQ ID NO 36
<211> LENGTH: 18
<212> TYPE: PRT
<213> ORGANISM: Artificial sequence
<220> FEATURE:
<223> OTHER INFORMATION: complementarity determining region (CDR) amino
      acid sequence

<400> SEQUENCE: 36

Ala Arg Gly Asp Tyr Tyr Tyr Asp Gly Val Ala Ser Asp Pro His Phe
1               5                   10                  15

Asp Asn

<210> SEQ ID NO 37
<211> LENGTH: 110
<212> TYPE: PRT
<213> ORGANISM: Artificial sequence
<220> FEATURE:
<223> OTHER INFORMATION: P4-170 IgL amino acid sequence

<400> SEQUENCE: 37

Gln Ser Val Leu Thr Gln Thr Pro Ser Ala Ser Gly Thr Pro Gly Gln
1               5                   10                  15

Arg Val Thr Ile Ser Cys Ser Gly Ser Arg Ser Asn Ile Gly Ser Asn
                20                  25                  30

Tyr Val Tyr Trp Phe Gln Gln Phe Pro Gly Ala Ala Pro Gln Leu Leu
            35                  40                  45

Ile Tyr Arg Asn Ile Gln Arg Pro Ser Gly Val Pro Ala Arg Phe Ser
        50                  55                  60

Gly Ser Lys Ser Asp Thr Ser Ala Ser Leu Ala Ile Ser Gly Leu Arg
65                  70                  75                  80

Ser Glu Asp Glu Ala His Tyr Tyr Cys Ala Ala Trp Asp Asp Ser Leu
                85                  90                  95

Ser Gly Val Val Phe Gly Gly Gly Thr Lys Val Thr Val Leu
            100                 105                 110

<210> SEQ ID NO 38
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 38

Arg Ser Asn Ile Gly Ser Asn Tyr
1               5

<210> SEQ ID NO 39
<211> LENGTH: 3
<212> TYPE: PRT
<213> ORGANISM: Artificial sequence
<220> FEATURE:
<223> OTHER INFORMATION: complementarity determining region (CDR) amino
     acid sequence

<400> SEQUENCE: 39

Arg Asn Ile
1

<210> SEQ ID NO 40
<211> LENGTH: 11
<212> TYPE: PRT
<213> ORGANISM: Artificial sequence
<220> FEATURE:
<223> OTHER INFORMATION: complementarity determining region (CDR) amino
     acid sequence

<400> SEQUENCE: 40

Ala Ala Trp Asp Asp Ser Leu Ser Gly Val Val
1               5               10

<210> SEQ ID NO 41
<211> LENGTH: 125
<212> TYPE: PRT
<213> ORGANISM: Artificial sequence
<220> FEATURE:
<223> OTHER INFORMATION: P4-66 IgH amino acid sequence

<400> SEQUENCE: 41

Glu Val Gln Leu Val Glu Ser Gly Gly Gly Leu Val Lys Pro Gly Gly
1               5               10             15

Ser Leu Arg Leu Ser Cys Ala Ala Ser Gly Phe Thr Phe Ser Ser His
       20           25          30

Arg Met His Trp Val Arg Gln Ala Pro Gly Lys Gly Leu Glu Trp Val
       35           40          45

Ser Ser Ile Ile Ser Ser Arg Thr Tyr Ile Tyr Tyr Ala Asp Ser Val
   50           55          60

Lys Gly Arg Phe Thr Ile Ser Arg Asp Asn Ser Gly Asn Ser Leu Phe
65               70          75          80

Leu Gln Met Asn Ser Leu Arg Val Glu Asp Thr Ala Val Tyr Tyr Cys
       85           90          95

Ala Arg Gly Asp Tyr Tyr Tyr Asp Gly Val Ala Ser Asp Pro His Phe
       100         105        110

Asp Asn Trp Gly Gln Gly Thr Leu Val Thr Val Ser Ser
       115         120        125

<210> SEQ ID NO 42
<211> LENGTH: 8
<212> TYPE: PRT
<213> ORGANISM: Artificial sequence
<220> FEATURE:
<223> OTHER INFORMATION: complementarity determining region (CDR) amino
     acid sequence

<400> SEQUENCE: 42

Gly Phe Thr Phe Ser Ser His Arg
1               5

-continued

```
<210> SEQ ID NO 43
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 43

Ile Ile Ser Ser Arg Thr Tyr Ile
1               5

<210> SEQ ID NO 44
<211> LENGTH: 18
<212> TYPE: PRT
<213> ORGANISM: Artificial sequence
<220> FEATURE:
<223> OTHER INFORMATION: complementarity determining region (CDR) amino
      acid sequence

<400> SEQUENCE: 44

Ala Arg Gly Asp Tyr Tyr Tyr Asp Gly Val Ala Ser Asp Pro His Phe
1               5                   10                  15

Asp Asn

<210> SEQ ID NO 45
<211> LENGTH: 110
<212> TYPE: PRT
<213> ORGANISM: Artificial sequence
<220> FEATURE:
<223> OTHER INFORMATION: P4-66 IgLamino acid sequence

<400> SEQUENCE: 45

Gln Ser Val Leu Thr Gln Thr Pro Ser Ala Ser Gly Thr Pro Gly Gln
1               5                   10                  15

Arg Val Thr Ile Ser Cys Ser Gly Ser Arg Ser Asn Ile Gly Ser Asn
                20                  25                  30

Tyr Val Tyr Trp Phe Gln Gln Phe Pro Gly Ala Ala Pro Gln Leu Leu
            35                  40                  45

Ile Tyr Arg Asn Ile Gln Arg Pro Ser Gly Val Pro Ala Arg Phe Ser
    50                  55                  60

Gly Ser Lys Ser Asp Thr Ser Ala Ser Leu Ala Ile Ser Gly Leu Arg
65                  70                  75                  80

Ser Glu Asp Glu Ala His Tyr Tyr Cys Ala Ala Trp Asp Asp Ser Leu
                85                  90                  95

Ser Gly Val Val Phe Gly Gly Gly Thr Lys Val Thr Val Leu
                100                 105                 110

<210> SEQ ID NO 46
<211> LENGTH: 6
<212> TYPE: PRT
<213> ORGANISM: Artificial sequence
<220> FEATURE:
<223> OTHER INFORMATION: complementarity determining region (CDR) amino
      acid sequence

<400> SEQUENCE: 46

Arg Ser Asn Ile Gly Ser
1               5

<210> SEQ ID NO 47
<211> LENGTH: 3
<212> TYPE: PRT
```

<213> ORGANISM: Artificial sequence
<220> FEATURE:
<223> OTHER INFORMATION: complementarity determining region (CDR) amino
      acid sequence

<400> SEQUENCE: 47

Arg Asn Ile
1

<210> SEQ ID NO 48
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 48

Ala Ala Trp Asp Asp Ser Leu Ser Gly Val Val
1               5                   10

<210> SEQ ID NO 49
<211> LENGTH: 125
<212> TYPE: PRT
<213> ORGANISM: Artificial sequence
<220> FEATURE:
<223> OTHER INFORMATION: P4-9 IgHamino acid sequence

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Arg Met His Trp Val Arg Gln Ala Pro Gly Lys Gly Leu Glu Trp Val
        35                  40                  45

Ser Ser Ile Ile Ser Ser Arg Thr Tyr Ile Tyr Tyr Ala Asp Ser Val
    50                  55                  60

Lys Gly Arg Phe Thr Ile Ser Arg Asp Asp Ser Arg Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Tyr Asp Gly Val Ala Ser Asp Pro His Phe
            100                 105                 110

Asp Asn Trp Gly Gln Gly Thr Leu Val Thr Val Ser Ser
        115                 120                 125

<210> SEQ ID NO 50
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 50

Gly Phe Thr Phe Ser Ser His Arg
1               5

<210> SEQ ID NO 51
<211> LENGTH: 8
<212> TYPE: PRT
<213> ORGANISM: Artificial sequence
<220> FEATURE:
<223> OTHER INFORMATION: complementarity determining region (CDR) amino acid sequence

<400> SEQUENCE: 51

Ile Ile Ser Ser Arg Thr Tyr Ile
1               5

<210> SEQ ID NO 52
<211> LENGTH: 18
<212> TYPE: PRT
<213> ORGANISM: Artificial sequence
<220> FEATURE:
<223> OTHER INFORMATION: complementarity determining region (CDR) amino
      acid sequence

<400> SEQUENCE: 52

Ala Arg Gly Asp Tyr Tyr Tyr Asp Gly Val Ala Ser Asp Pro His Phe
1               5                   10                  15

Asp Asn

<210> SEQ ID NO 53
<211> LENGTH: 110
<212> TYPE: PRT
<213> ORGANISM: Artificial sequence
<220> FEATURE:
<223> OTHER INFORMATION: P4-9 IgL amino acid sequence

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Tyr Val Tyr Trp Phe Gln Gln Leu Pro Gly Thr Ala Pro Gln Leu Leu
        35                  40                  45

Ile Tyr Arg Asn Ile Gln Arg Pro Ser Gly Val Pro Ala Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Val Thr Val Leu
            100                 105                 110

<210> SEQ ID NO 54
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 54

Arg Ser Asn Ile Gly Ser Asn Tyr
1               5

<210> SEQ ID NO 55
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 55

-continued

```
Arg Asn Ile
1

<210> SEQ ID NO 56
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 56

Ala Ala Trp Asp Asp Ser Leu Ser Gly Val Val
1               5                   10

<210> SEQ ID NO 57
<211> LENGTH: 118
<212> TYPE: PRT
<213> ORGANISM: Artificial sequence
<220> FEATURE:
<223> OTHER INFORMATION: P4-141 IgH amino acid sequence

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Thr Phe Thr Phe Asn Ser Tyr
            20                  25                  30

Trp Met His Trp Val Arg Gln Ala Pro Gly Lys Gly Leu Val Trp Val
        35                  40                  45

Ser Leu Ile Asn Pro Asp Gly Ser Thr Thr Lys Ser Ala Asp Ser Val
    50                  55                  60

Lys Gly Arg Phe Thr Ile Ser Arg Asp Asn Ala Glu Asn Thr Leu Tyr
65                  70                  75                  80

Leu Gln Met Asn Ser Leu Arg Ala Glu Asp Thr Ala Ile Tyr Tyr Cys
                85                  90                  95

Ala Gly Ala Tyr Ser Ser Gly Trp Tyr Lys Arg Trp Gly Gln Gly Thr
            100                 105                 110

Leu Val Thr Val Ser Ser
        115

<210> SEQ ID NO 58
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 58

Thr Phe Thr Phe Asn Ser Tyr Trp
1               5

<210> SEQ ID NO 59
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 59

Ile Asn Pro Asp Gly Ser Thr Thr
1               5
```

```
<210> SEQ ID NO 60
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 60

Ala Gly Ala Tyr Ser Ser Gly Trp Tyr Lys Arg
1               5                   10

<210> SEQ ID NO 61
<211> LENGTH: 107
<212> TYPE: PRT
<213> ORGANISM: Artificial sequence
<220> FEATURE:
<223> OTHER INFORMATION: P4-141 IgL amino acid sequence

<400> SEQUENCE: 61

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Gly Ile Ser Arg Ser
                20                  25                  30

Leu Ala Trp Tyr Gln Gln Lys Pro Gly Lys Ala Pro Gln Leu Leu Leu
        35                  40                  45

Tyr Gly Ala Ser Arg Leu Glu Ser Gly Val Pro Ser Arg Phe Ser Gly
    50                  55                  60

Thr Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Asn Val Pro Tyr
                85                  90                  95

Thr Phe Gly Gln Gly Thr Lys Leu Glu Ile Lys
            100                 105

<210> SEQ ID NO 62
<211> LENGTH: 6
<212> TYPE: PRT
<213> ORGANISM: Artificial sequence
<220> FEATURE:
<223> OTHER INFORMATION: complementarity determining region (CDR) amino
      acid sequence

<400> SEQUENCE: 62

Gln Gly Ile Ser Arg Ser
1               5

<210> SEQ ID NO 63
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 63

Gly Ala Ser
1

<210> SEQ ID NO 64
<211> LENGTH: 9
<212> TYPE: PRT
<213> ORGANISM: Artificial sequence
<220> FEATURE:
```

<223> OTHER INFORMATION: complementarity determining region (CDR) amino
       acid sequence

<400> SEQUENCE: 64

Gln Gln Tyr Tyr Asn Val Pro Tyr Thr
1               5

<210> SEQ ID NO 65
<211> LENGTH: 118
<212> TYPE: PRT
<213> ORGANISM: Artificial sequence
<220> FEATURE:
<223> OTHER INFORMATION: P4-48 IgH amino acid sequence

<400> SEQUENCE: 65

Glu Val Gln Leu Val Gln Ser Gly Gly Gly Leu Val Gln Pro Gly Gly
1               5                   10                  15

Ser Leu Arg Leu Ser Cys Ala Ala Ser Thr Phe Thr Phe Ser Ser Tyr
            20                  25                  30

Trp Met His Trp Val Arg Gln Ala Pro Gly Lys Gly Leu Val Trp Val
        35                  40                  45

Ser Leu Ile Asn Pro Asp Gly Ser Thr Thr Lys Ser Ala Asp Ser Val
    50                  55                  60

Lys Gly Arg Phe Thr Ile Ser Arg Asp Asn Ala Glu Asn Thr Leu Tyr
65                  70                  75                  80

Leu Gln Met Asn Ser Leu Arg Ala Asp Asp Thr Ala Ile Tyr Tyr Cys
                85                  90                  95

Ala Gly Ala Tyr Ser Ser Gly Trp Tyr Lys Arg Trp Gly Gln Gly Thr
            100                 105                 110

Leu Val Ala Val Ser Ser
        115

<210> SEQ ID NO 66
<211> LENGTH: 8
<212> TYPE: PRT
<213> ORGANISM: Artificial sequence
<220> FEATURE:
<223> OTHER INFORMATION: complementarity determining region (CDR) amino
       acid sequence

<400> SEQUENCE: 66

Thr Phe Thr Phe Ser Ser Tyr Trp
1               5

<210> SEQ ID NO 67
<211> LENGTH: 8
<212> TYPE: PRT
<213> ORGANISM: Artificial sequence
<220> FEATURE:
<223> OTHER INFORMATION: complementarity determining region (CDR) amino
       acid sequence

<400> SEQUENCE: 67

Ile Asn Pro Asp Gly Ser Thr Thr
1               5

<210> SEQ ID NO 68
<211> LENGTH: 11
<212> TYPE: PRT
<213> ORGANISM: Artificial sequence
<220> FEATURE:
<223> OTHER INFORMATION: complementarity determining region (CDR) amino
       acid sequence

<400> SEQUENCE: 68

Ala Gly Ala Tyr Ser Ser Gly Trp Tyr Lys Arg
1               5                   10

<210> SEQ ID NO 69
<211> LENGTH: 118
<212> TYPE: PRT
<213> ORGANISM: Artificial sequence
<220> FEATURE:
<223> OTHER INFORMATION: P4-85 IgH amino acid sequence

<400> SEQUENCE: 69

Glu Val Gln Leu Val Gln Ser Gly Gly Gly Leu Val Gln Pro Gly Gly
1               5                   10                  15

Ser Leu Arg Leu Ser Cys Ala Ala Ser Thr Phe Thr Phe Ser Ser Tyr
            20                  25                  30

Trp Met His Trp Val Arg Gln Ala Pro Gly Lys Gly Leu Val Trp Val
        35                  40                  45

Ser Leu Ile Asn Pro Asp Gly Ser Thr Thr Lys Ser Ala Asp Ser Val
    50                  55                  60

Lys Gly Arg Phe Thr Ile Ser Arg Asp Asn Ala Glu Asn Thr Leu Tyr
65                  70                  75                  80

Leu Gln Met Asn Ser Leu Arg Ala Glu Asp Thr Ala Ile Tyr Tyr Cys
            85                  90                  95

Ala Gly Ala Tyr Ser Ser Gly Trp Tyr Lys Arg Trp Gly Gln Gly Thr
            100                 105                 110

Leu Val Ala Val Ser Ser
        115

<210> SEQ ID NO 70
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 70

Ile Asn Pro Asp Gly Ser Thr Thr
1               5

<210> SEQ ID NO 71
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 71

Thr Phe Thr Phe Ser Ser Tyr Trp
1               5

<210> SEQ ID NO 72
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 72

Ala Gly Ala Tyr Ser Ser Gly Trp Tyr Lys Arg

```
1               5                  10
```

```
<210> SEQ ID NO 73
<211> LENGTH: 128
<212> TYPE: PRT
<213> ORGANISM: Artificial sequence
<220> FEATURE:
<223> OTHER INFORMATION: P4-107 IgH amino acid sequence

<400> SEQUENCE: 73

Glu Val Gln Leu Val Glu Ser Gly Gly Gly Leu Val Gln Pro Gly Arg
1               5                  10                  15

Ser Leu Arg Leu Ser Cys Thr Asp Ser Gly Phe Thr Phe Ser Glu Tyr
            20                  25                  30

Ala Leu Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Val
65                  70                  75                  80

Ala Tyr Leu Gln Met Asn Ser Leu Lys Thr Glu Asp Thr Ala Val Tyr
                85                  90                  95

Phe Cys Thr Gly Pro Arg Pro Tyr Tyr Asp Ser Ser Gly Tyr Tyr Pro
            100                 105                 110

Tyr Tyr Phe Asp Tyr Trp Gly Gln Gly Thr Leu Val Thr Val Ser Ser
        115                 120                 125

<210> SEQ ID NO 74
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 74

Gly Phe Thr Phe Ser Glu Tyr Ala
1               5

<210> SEQ ID NO 75
<211> LENGTH: 10
<212> TYPE: PRT
<213> ORGANISM: Artificial sequence
<220> FEATURE:
<223> OTHER INFORMATION: complementarity determining region (CDR) amino
      acid sequence

<400> SEQUENCE: 75

Ile Arg Ser Lys Ala Tyr Gly Gly Thr Thr
1               5                  10

<210> SEQ ID NO 76
<211> LENGTH: 19
<212> TYPE: PRT
<213> ORGANISM: Artificial sequence
<220> FEATURE:
<223> OTHER INFORMATION: complementarity determining region (CDR) amino
      acid sequence

<400> SEQUENCE: 76

Thr Gly Pro Arg Pro Tyr Tyr Asp Ser Ser Gly Tyr Tyr Pro Tyr Tyr
1               5                  10                  15

Phe Asp Tyr
```

-continued

```
<210> SEQ ID NO 77
<211> LENGTH: 111
<212> TYPE: PRT
<213> ORGANISM: Artificial sequence
<220> FEATURE:
<223> OTHER INFORMATION: P4-107 IgL amino acid sequence

<400> SEQUENCE: 77

Gln Ser Ala Leu Thr Gln Pro Arg Ser Val Ser Gly Ser Pro Gly Gln
1               5                   10                  15

Ser Val Thr Ile Ser Cys Thr Gly Ser Arg Ser Asp Val Gly Gly Tyr
                20                  25                  30

Asp Tyr Val Ser Trp Tyr Gln Gln His Pro Gly Arg Val Pro Lys Leu
            35                  40                  45

Met Ile Tyr Asp Val Thr Lys Arg Pro Ser Gly Val Pro Asp Arg Phe
        50                  55                  60

Ser Gly Ser Arg Ser Gly Asn Thr Ala Ser Leu Thr Ile Ser Gly Leu
65                  70                  75                  80

Gln Ala Asp Asp Glu Ala Asp Tyr Tyr Cys Ser Ser Phe Ala Gly Ser
                85                  90                  95

Ser Thr Tyr Val Val Phe Gly Gly Gly Thr Thr Leu Thr Val Leu
            100                 105                 110

<210> SEQ ID NO 78
<211> LENGTH: 9
<212> TYPE: PRT
<213> ORGANISM: Artificial sequence
<220> FEATURE:
<223> OTHER INFORMATION: complementarity determining region (CDR) amino
      acid sequence

<400> SEQUENCE: 78

Arg Ser Asp Val Gly Gly Tyr Asp Tyr
1               5

<210> SEQ ID NO 79
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 79

Asp Val Thr
1

<210> SEQ ID NO 80
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 80

Ser Ser Phe Ala Gly Ser Ser Thr Tyr Val Val
1               5                   10

<210> SEQ ID NO 81
<211> LENGTH: 128
<212> TYPE: PRT
<213> ORGANISM: Artificial sequence
```

-continued

```
<220> FEATURE:
<223> OTHER INFORMATION: P4-36 IgH amino acid sequence

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Thr Asp Ser Gly Phe Thr Phe Ser Glu Tyr
            20                  25                  30

Ala Leu Ser Trp Val Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Val
65                  70                  75                  80

Ala Tyr Leu Gln Met Asn Ser Leu Lys Thr Glu Asp Thr Ala Val Tyr
                85                  90                  95

Phe Cys Thr Gly Pro Arg Pro Tyr Tyr Asp Ser Ser Gly Tyr Tyr Pro
                100                 105                 110

Tyr Tyr Phe Asp Tyr Trp Gly Gln Gly Thr Leu Val Thr Val Ser Ser
        115                 120                 125

<210> SEQ ID NO 82
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 82

Gly Phe Thr Phe Ser Glu Tyr Ala
1               5

<210> SEQ ID NO 83
<211> LENGTH: 10
<212> TYPE: PRT
<213> ORGANISM: Artificial sequence
<220> FEATURE:
<223> OTHER INFORMATION: complementarity determining region (CDR) amino
      acid sequence

<400> SEQUENCE: 83

Ile Arg Ser Lys Ala Tyr Gly Gly Thr Thr
1               5                   10

<210> SEQ ID NO 84
<211> LENGTH: 19
<212> TYPE: PRT
<213> ORGANISM: Artificial sequence
<220> FEATURE:
<223> OTHER INFORMATION: complementarity determining region (CDR) amino
      acid sequence

<400> SEQUENCE: 84

Thr Gly Pro Arg Pro Tyr Tyr Asp Ser Ser Gly Tyr Tyr Pro Tyr Tyr
1               5                   10                  15

Phe Asp Tyr

<210> SEQ ID NO 85
<211> LENGTH: 111
<212> TYPE: PRT
<213> ORGANISM: Artificial sequence
<220> FEATURE:
```

<223> OTHER INFORMATION: P4-36 IgLamino acid sequence

<400> SEQUENCE: 85

Gln Ser Ala Leu Thr Gln Pro Arg Ser Val Ser Gly Ser Pro Gly Gln
1               5                   10                  15

Ser Val Thr Ile Ser Cys Thr Gly Ser Arg Ser Asp Val Gly Gly Tyr
                20                  25                  30

Asp Tyr Val Ser Trp Tyr Gln Gln His Pro Gly Arg Val Pro Lys Leu
            35                  40                  45

Met Ile Tyr Asp Val Thr Lys Arg Pro Ser Gly Val Pro Asp Arg Phe
        50                  55                  60

Ser Gly Ser Arg Ser Gly Asn Thr Ala Ser Leu Thr Ile Ser Gly Leu
65                  70                  75                  80

Gln Ala Asp Asp Glu Ala Asp Tyr Tyr Cys Ser Ser Phe Ala Gly Ser
                85                  90                  95

Ser Thr Tyr Val Val Phe Gly Gly Gly Thr Thr Leu Thr Val Leu
            100                 105                 110

<210> SEQ ID NO 86
<211> LENGTH: 9
<212> TYPE: PRT
<213> ORGANISM: Artificial sequence
<220> FEATURE:
<223> OTHER INFORMATION: complementarity determining region (CDR) amino
      acid sequence

<400> SEQUENCE: 86

Arg Ser Asp Val Gly Gly Tyr Asp Tyr
1               5

<210> SEQ ID NO 87
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 87

Asp Val Thr
1

<210> SEQ ID NO 88
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 88

Ser Ser Phe Ala Gly Ser Ser Thr Tyr Val Val
1               5                   10

<210> SEQ ID NO 89
<211> LENGTH: 120
<212> TYPE: PRT
<213> ORGANISM: Artificial sequence
<220> FEATURE:
<223> OTHER INFORMATION: P4-31 IgH amino acid sequence

<400> SEQUENCE: 89

Gln Val Gln Leu Val Gln Ser Gly Ala Glu Val Lys Asn Pro Gly Ala
1               5                   10                  15

```
Ser Val Lys Ile Ala Cys Val Ala Ser Gly His Asn Phe Ser Asp Phe
        20              25              30

Tyr Phe His Trp Val Arg Gln Ala Pro Gly Gln Gly Leu Glu Trp Met
        35              40              45

Gly Ile Val Lys Gly Gly Gly Val Thr Gly Tyr Pro Gln Arg Leu
    50              55              60

Lys Gly Arg Val Thr Met Thr Thr Asp Thr Ser Thr Arg Thr Ile Tyr
65              70              75              80

Leu Glu Leu Lys Asn Leu Thr Ser Asp Asp Thr Ala Thr Tyr Tyr Cys
            85              90              95

Ala Arg Asp Pro Gly Cys Asn Gly Gly Ser Cys Tyr Tyr Phe Asp His
        100             105             110

Trp Gly Arg Gly Thr Leu Val Thr
        115             120
```

```
<210> SEQ ID NO 90
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 90

Gly His Asn Phe Ser Asp Phe Tyr
1               5
```

```
<210> SEQ ID NO 91
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 91

Val Lys Gly Gly Gly Gly Val Thr
1               5
```

```
<210> SEQ ID NO 92
<211> LENGTH: 16
<212> TYPE: PRT
<213> ORGANISM: Artificial sequence
<220> FEATURE:
<223> OTHER INFORMATION: complementarity determining region (CDR) amino
      acid sequence

<400> SEQUENCE: 92

Ala Arg Asp Pro Gly Cys Asn Gly Gly Ser Cys Tyr Tyr Phe Asp His
1               5               10              15
```

```
<210> SEQ ID NO 93
<211> LENGTH: 108
<212> TYPE: PRT
<213> ORGANISM: Artificial sequence
<220> FEATURE:
<223> OTHER INFORMATION: P4-31 IgLamino acid sequence

<400> SEQUENCE: 93

Ser Tyr Glu Leu Thr Gln Ser Thr Ser Met Ser Val Ser Pro Gly Gln
1               5               10              15

Thr Ala Thr Ile Thr Cys Ser Gly Asp Ala Leu Pro Lys Gln Tyr Ala
        20              25              30
```

-continued

```
Tyr Trp Tyr Gln Gln Lys Ser Gly Gln Ala Pro Thr Leu Leu Ile Tyr
        35              40              45

Lys Asp Asn Gln Arg Ser Ser Gly Ile Pro Asp Arg Phe Ser Gly Ser
    50              55              60

Ser Ser Gly Thr Thr Leu Thr Leu Thr Ile Ser Gly Val Gln Thr Glu
65              70              75              80

Asp Glu Ala Val Tyr His Cys Gln Ser Ser Asp Ile Thr Ser Arg Phe
                85              90              95

Val Ile Phe Gly Gly Gly Thr Lys Leu Thr Val Leu
            100             105

<210> SEQ ID NO 94
<211> LENGTH: 6
<212> TYPE: PRT
<213> ORGANISM: Artificial sequence
<220> FEATURE:
<223> OTHER INFORMATION: complementarity determining region (CDR) amino
      acid sequence

<400> SEQUENCE: 94

Ala Leu Pro Lys Gln Tyr
1               5

<210> SEQ ID NO 95
<211> LENGTH: 3
<212> TYPE: PRT
<213> ORGANISM: Artificial sequence
<220> FEATURE:
<223> OTHER INFORMATION: complementarity determining region (CDR) amino
      acid sequence

<400> SEQUENCE: 95

Lys Asp Asn
1

<210> SEQ ID NO 96
<211> LENGTH: 11
<212> TYPE: PRT
<213> ORGANISM: Artificial sequence
<220> FEATURE:
<223> OTHER INFORMATION: complementarity determining region (CDR) amino
      acid sequence

<400> SEQUENCE: 96

Gln Ser Ser Asp Ile Thr Ser Arg Phe Val Ile
1               5               10

<210> SEQ ID NO 97
<211> LENGTH: 122
<212> TYPE: PRT
<213> ORGANISM: Artificial sequence
<220> FEATURE:
<223> OTHER INFORMATION: P4-62 IgH amino acid sequence

<400> SEQUENCE: 97

Val Gln Leu Val Gln Ser Gly Ala Glu Val Lys Lys Pro Gly Ala Ser
1               5               10              15

Leu Arg Leu Ala Cys Thr Ala Ser Gly Tyr Asn Phe Ser Asp Phe Tyr
            20              25              30

Ile His Trp Val Arg Gln Ala Pro Gly Gln Gly Leu Glu Trp Met Gly
        35              40              45

Ile Val Lys Gly Gly Gly Gly Val Thr Gly Tyr Pro Gln Ala Leu Arg
    50              55              60
```

```
Ser Arg Val Thr Met Thr Thr Asp Thr Ser Thr Thr Thr Val Tyr Met
65              70              75              80

Glu Leu Lys Asn Ile Ser Ser Glu Asp Thr Ala Ile Tyr Tyr Cys Ala
                85              90              95

Arg Asp Pro Gly Cys Asn Gly Gly Ser Cys Tyr Tyr Phe Asp His Trp
        100             105             110

Gly Arg Gly Thr Leu Val Thr Val Ser Ser
        115             120

<210> SEQ ID NO 98
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 98

Gly Tyr Asn Phe Ser Asp Phe Tyr
1               5

<210> SEQ ID NO 99
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 99

Val Lys Gly Gly Gly Gly Val Thr
1               5

<210> SEQ ID NO 100
<211> LENGTH: 16
<212> TYPE: PRT
<213> ORGANISM: Artificial sequence
<220> FEATURE:
<223> OTHER INFORMATION: complementarity determining region (CDR) amino
      acid sequence

<400> SEQUENCE: 100

Ala Arg Asp Pro Gly Cys Asn Gly Gly Ser Cys Tyr Tyr Phe Asp His
1               5               10              15

<210> SEQ ID NO 101
<211> LENGTH: 126
<212> TYPE: PRT
<213> ORGANISM: Artificial sequence
<220> FEATURE:
<223> OTHER INFORMATION: P4-13 IgH amino acid sequence

<400> SEQUENCE: 101

Val Gln Leu Val Gln Ser Gly Gly Gly Leu Val Lys Pro Gly Gly Ser
1               5               10              15

Leu Arg Leu Ser Cys Ala Ala Ser Gly Phe Thr Phe Ser Asp Tyr Tyr
                20              25              30

Met Ser Trp Ile Arg Gln Ala Pro Gly Lys Gly Leu Glu Trp Val Ser
        35              40              45

Tyr Ile Ser Ser Ser Gly Gly Thr Val Tyr Tyr Ala Asp Ser Val Lys
    50              55              60

Gly Arg Phe Thr Ile Ser Arg Asp Asn Ala Asn Asn Ala Leu Tyr Leu
65              70              75              80
```

Gln Met Asn Ser Leu Arg Ala Glu Asp Thr Ala Val Tyr Phe Cys Ala
            85                  90                  95

Arg Asp Leu Asp Ser Ala Ser Trp Ser Gly Tyr Tyr Tyr Tyr Ser
            100                 105                 110

Met Tyr Val Trp Gly Gln Gly Thr Thr Val Thr Val Ser Ser
        115                 120                 125

<210> SEQ ID NO 102
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 102

Gly Phe Thr Phe Ser Asp Tyr Tyr
1               5

<210> SEQ ID NO 103
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 103

Ile Ser Ser Ser Gly Gly Thr Val
1               5

<210> SEQ ID NO 104
<211> LENGTH: 20
<212> TYPE: PRT
<213> ORGANISM: Artificial sequence
<220> FEATURE:
<223> OTHER INFORMATION: complementarity determining region (CDR) amino
      acid sequence

<400> SEQUENCE: 104

Ala Arg Asp Leu Asp Ser Ala Ser Trp Ser Gly Tyr Tyr Tyr Tyr Tyr
1               5                   10                  15

Ser Met Tyr Val
            20

<210> SEQ ID NO 105
<211> LENGTH: 126
<212> TYPE: PRT
<213> ORGANISM: Artificial sequence
<220> FEATURE:
<223> OTHER INFORMATION: P4-67 IgH amino acid sequence

<400> SEQUENCE: 105

Val Gln Leu Val Gln Ser Gly Gly Gly Leu Val Lys Pro Gly Gly Ser
1               5                   10                  15

Leu Arg Leu Ser Cys Ala Ala Ser Gly Phe Thr Phe Ser Asp Tyr Tyr
            20                  25                  30

Met Ser Trp Ile Arg Gln Ala Pro Gly Lys Gly Gln Glu Trp Val Ser
        35                  40                  45

Tyr Ile Ser Ser Ser Gly Gly Thr Val Tyr Tyr Ala Asp Ser Gly Lys
    50                  55                  60

Gly Arg Phe Thr Ile Ser Arg Asp Asn Ala Asn Asn Gly Gln Tyr Gln
65                  70                  75                  80

Gln Met Asn Ser Glu Arg Ala Glu Asp Thr Ala Val Tyr Phe Cys Ala
            85                  90                  95

Arg Asp Val Asp Ser Ala Ser Trp Ser Gly Tyr Tyr Tyr Tyr Ser
            100                 105                 110

Met Tyr Val Trp Gly Gln Gly Thr Thr Val Thr Val Ser Ser
        115                 120                 125

<210> SEQ ID NO 106
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 106

Gly Phe Thr Phe Ser Asp Tyr Tyr
1               5

<210> SEQ ID NO 107
<211> LENGTH: 8
<212> TYPE: PRT
<213> ORGANISM: Artificial sequence
<220> FEATURE:
<223> OTHER INFORMATION: complementarity determining region (CDR) amino
      acid sequence

<400> SEQUENCE: 107

Ile Ser Ser Ser Gly Gly Thr Val
1               5

<210> SEQ ID NO 108
<211> LENGTH: 20
<212> TYPE: PRT
<213> ORGANISM: Artificial sequence
<220> FEATURE:
<223> OTHER INFORMATION: complementarity determining region (CDR) amino
      acid sequence

<400> SEQUENCE: 108

Ala Arg Asp Val Asp Ser Ala Ser Trp Ser Gly Tyr Tyr Tyr Tyr
1               5                   10                  15

Ser Met Tyr Val
            20

<210> SEQ ID NO 109
<211> LENGTH: 370
<212> TYPE: DNA
<213> ORGANISM: Artificial sequence
<220> FEATURE:
<223> OTHER INFORMATION: P4-31 HC

<400> SEQUENCE: 109
ccaggtgcag ctggtgcagt ctggggccga ggtgaagaac cctggggcct cagtgaaaat      60
tgcctgcgtg gcatctgggc acaacttcag cgacttctat ttccactggg tgcgacaggc     120
ccctggacaa ggcctggaat ggatgggaat tgtcaaagga ggtggtggtg tcacaggata     180
cccacagagg ttgaagggtc gagtcaccat gaccacagac acgtccacga gaacaatcta     240
tctggaactg aaaaatttaa cttctgacga cacggccact tattattgtg cgagagaccc     300
tggatgtaat ggtgggagct gttattattt tgaccattgg ggccggggaa ccctggtcac     360
cgtctcctca                                                           370

-continued

```
<210> SEQ ID NO 110
<211> LENGTH: 324
<212> TYPE: DNA
<213> ORGANISM: Artificial sequence
<220> FEATURE:
<223> OTHER INFORMATION: P4-31 LC nucleic acid sequence

<400> SEQUENCE: 110
tcctatgagc tgactcagtc aacctcgatg tctgtgtccc caggacagac ggccacgatc      60
acctgctctg gagatgcatt gccgaaacaa tatgcttatt ggtaccagca gaagtcaggc     120
caggccccaa ctttgctgat atataaagac aatcagaggt cttcagggat ccctgaccgg     180
ttctctggct ccagctcagg gacaacactc accttgacca tcagtggagt ccagacagag     240
gacgaggctg tctatcactg tcaatcatct gacatcacta gtcgttttgt gattttcggc     300
ggagggacca aactgaccgt cctg                                            324

<210> SEQ ID NO 111
<211> LENGTH: 385
<212> TYPE: DNA
<213> ORGANISM: Artificial sequence
<220> FEATURE:
<223> OTHER INFORMATION: P4-36 HC nucleic acid sequence

<400> SEQUENCE: 111
gaggtgcagc tggtggagtc tggggggaggc ttggtacagc cagggcggtc cctgagactc      60
tcctgtacag actctggatt cacctttagt gaatatgctc tgagctgggt acgccaggct     120
ccagggaagg ggctggagtg ggtcggtttc attagaagca aagcttatgg tgggacaaca     180
gaatacgccg cgtctgtgaa gggcagattc accatctcaa gagatgattc caaaagtgtc     240
gcctatctgc agatgaacag cctgaaaacc gaggacacac ccgtgtattt ctgtactggg     300
cctcggcctt attatgatag tagcggttat tacccgtatt attttgacta ctggggccag     360 ggaacccctgg tcaccgtctc ctcag                                          385

<210> SEQ ID NO 112
<211> LENGTH: 333
<212> TYPE: DNA
<213> ORGANISM: Artificial sequence
<220> FEATURE:
<223> OTHER INFORMATION: P4-36 LC nucleic acid sequence

<400> SEQUENCE: 112
cagtctgccc tgactcagcc tcgctcagtg tccgggtctc ctggacagtc agtcaccatc      60
tcctgcactg gcagcaggag tgatgtcggt ggttatgact atgtctcctg gtaccaacag     120
cacccaggca gagtccccaa actcatgatt tatgatgtca ctaagcggcc ctctggggtc     180
cctgatcgct tctctggctc caggtctggc aacacggcct ccctgaccat ctctgggctc     240
caggctgacg atgaggctga ttattactgc tcctcatttg caggcagctc cacttatgtg     300
gttttcggcg gcgggaccac gctgaccgtc cta                                  333

<210> SEQ ID NO 113
<211> LENGTH: 354
<212> TYPE: DNA
<213> ORGANISM: Artificial sequence
<220> FEATURE:
<223> OTHER INFORMATION: P4-48 HC nucleic acid sequence

<400> SEQUENCE: 113
gaggtgcagc tggtggagtc cggggggaggc ttagttcagc ctggggggtc cctgagactc      60
```

-continued

```
tcctgtgcag cctccacatt cactttcagt agctactgga tgcactgggt ccgccaagct    120
ccagggaagg gactggtgtg ggtgtcactt attaatcctg atggcagtac cacgaagtcc    180
gcggactccg tgaagggccg attcaccatc tccagagaca cgccgagaa cactttgtat     240 ctgcaaatga acagtctgag agccgacgac acagctatat attactgcgc cggagcttat    300
agcagtggct ggtataagag gtggggccag ggaaccctgg tcaccgtctc ctca          354

<210> SEQ ID NO 114
<211> LENGTH: 360
<212> TYPE: DNA
<213> ORGANISM: Artificial sequence
<220> FEATURE:
<223> OTHER INFORMATION: P4-62 HC nucleic acid sequence

<400> SEQUENCE: 114
caggtgcagc tggtgcagtc tggggccgag gtgaagaagc ctggggcctc actgagactt     60
gcctgcacgg catctggata caacttcagc gacttctata tacactgggt gcgacaggcc    120
cctggacaag ggctggagtg gatgggaatc gtcaaggag gtggtggtgt cacgggctac      180
ccacaggcgt tgcggagtag agtcaccatg accacagaca cgtccacgac tacagtctat    240
atggaattga agaatataag ttctgaagat acggccattt attattgtgc gagagaccct    300
ggatgtaatg gtgggagttg ttactacttt gaccattggg ccggggaac cctggtcacc     360

<210> SEQ ID NO 115
<211> LENGTH: 376
<212> TYPE: DNA
<213> ORGANISM: Artificial sequence
<220> FEATURE:
<223> OTHER INFORMATION: P4-66 HC nucleic acid sequence

<400> SEQUENCE: 115
gaggtgcagc tggtggagtc gggggggaggc ctggtcaagc cggggggggtc cctgagactc    60 tcctgtgcag cctccggatt caccttcagt agccatagga tgcactgggt ccgccaggct    120
ccagggaagg ggctggagtg ggtctcatcc attattagta gtcgaactta tatatactat    180
gcagactcag tgaagggccg attcaccatc tccagagaca actccgggaa ctcactgttt    240
ctgcaaatga acagcctgag agtcgaggac acggctgttt attactgtgc gcgaggagac    300
tactactatg atggtgttgc ctcagaccct cactttgaca ctggggcca gggaaccctg    360 gtcaccgtct cctcag                                                     376

<210> SEQ ID NO 116
<211> LENGTH: 330
<212> TYPE: DNA
<213> ORGANISM: Artificial sequence
<220> FEATURE:
<223> OTHER INFORMATION: P4-66 LC nucleic acid sequence

<400> SEQUENCE: 116
cagtctgtgc tgactcagac accctcagcg tctgggaccc ccgggcagag ggtcaccatc     60
tcttgttctg gcagcaggtc caacattgga agtaattacg tatactggtt ccagcagttc    120
ccaggagcgg ccccccaact cctcatctat aggaatattt agcggccctc aggggtccct    180
gcccgattct ctggctccaa gtctgacacc tcagcctcac tggccatcag tggactccgg    240
tccgaggatg aggctcatta ttactgtgca gcatgggatg acagcctgag tggtgtggtt    300
ttcggcggag ggaccaaggt gaccgtccta                                      330
```

<210> SEQ ID NO 117
<211> LENGTH: 354
<212> TYPE: DNA
<213> ORGANISM: Artificial sequence
<220> FEATURE:
<223> OTHER INFORMATION: P4-85 HC nucleic acid sequence

<400> SEQUENCE: 117
gaggtgcagc tggtggagtc cggggggaggc ttagttcagc ctggggggtc cctgagactc      60
tcctgtgcag cctccacatt cactttcagt agctactgga tgcactgggt ccgccaagct     120
ccagggaagg ggctggtgtg ggtgtcactt attaatcctg atggcagtac cacaaagtcc     180
gcggactccg tgaagggccg attcaccatc tccagagaca cgccgagaa cactttgtat      240 ctgcaaatga acagtctgag agccgaggac acagctatat attactgcgc cggagcttat     300
agcagtggct ggtataagag gtggggccag ggaaccctgg tcaccgtctc ctca           354

<210> SEQ ID NO 118
<211> LENGTH: 385
<212> TYPE: DNA
<213> ORGANISM: Artificial sequence
<220> FEATURE:
<223> OTHER INFORMATION: P4-107 HC nucleic acid sequence

<400> SEQUENCE: 118
tgaggtgcag ctggtggagt ctggggggagg cttggtacag ccagggcggt ccctgagact      60
ctcctgtaca gactctggat tcacctttag tgaatatgct ctgagctggg tacgccaggc     120
tccagggaag gggctggagt gggtcggttt cattagaagc aaagcttatg gtgggacaac     180
agaatacgcc gcgtctgtga agggcagatt caccatctca agagatgatt ccaaaagtgt     240
cgcctatctg caaatgaaca gcctgaaaac cgaggacaca gccgtgtatt tctgtactgg     300
gcctcggcct tattatgata gtagcggtta ttacccgtat tattttgact actggggcca     360
gggaaccctg gtcaccgtct cctca                                           385

<210> SEQ ID NO 119
<211> LENGTH: 333
<212> TYPE: DNA
<213> ORGANISM: Artificial sequence
<220> FEATURE:
<223> OTHER INFORMATION: P4-107 LC nucleic acid sequence

<400> SEQUENCE: 119
cagtctgccc tgactcagcc tcgctcagtg tccgggtctc ctggacagtc agtcaccatc      60
tcctgcactg gcagcaggag tgatgtcggt ggttatgact atgtctcctg gtaccaacag     120
cacccaggca gagtccccaa actcatgatt tatgatgtca ctaagcggcc ctctggggtc     180
cctgatcgct tctctggctc caggtctggc aacacggcct ccctgaccat ctctgggctc     240
caggctgacg atgaggctga ttattactgc tcctcatttg cagacagctc cacttatgtg     300
gttttcggcg gcgggaccac gctgaccgtc cta                                  333

<210> SEQ ID NO 120
<211> LENGTH: 375
<212> TYPE: DNA
<213> ORGANISM: Artificial sequence
<220> FEATURE:
<223> OTHER INFORMATION: P4-123 HC nucleic acid sequence

<400> SEQUENCE: 120
gaggtgcagc tggtggagtc tggggggaggc ctggtcaagc cggggggggtc cctgagactc      60

-continued

```
tcctgtgcag cctctggatt caccttcgaa agccatagga tgcactgggt ccgccaggct      120
ccagggaagg ggctagaatg ggtctcatcc attattagta gtcgaactta catatactac      180
gcagactcag tgaagggccg attcaccatc tccagagaca actccaggaa ctcactcttt      240
ctacaaatga acagcctgag agccgaggac acggctgtgt attactgtgc acgaggagac      300
tactactatg atggtgttgc ctcagatcct cactttgaca actggggcca gggaaccctg      360
gtcaccgtct cctca                                                       375
```

<210> SEQ ID NO 121
<211> LENGTH: 330
<212> TYPE: DNA
<213> ORGANISM: Artificial sequence
<220> FEATURE:
<223> OTHER INFORMATION: P4-123 LC nucleic acid sequence

<400> SEQUENCE: 121

```
cagtctgtgc tgacgcagcc accctcagcg tctgggaccc ccggtcagag ggtcaccatc       60
tcttgttctg gcggcaggtc caacatcgga agtaattatg tatactggtt ccagcagctc      120
ccaggaacgg cccccaact cctcatctat aggaatattc agcggccctc aggggtccct      180
gcccgattct ctggctccaa gtctggcacc tcagcctcac tggccatcag tgggctccgg      240
tccgaggatg aggctgatta ttactgtgca acatgggatg acagcctgag tggtgtggtt      300
ttcggcggag ggaccaaggt gaccgtccta                                       330
```

<210> SEQ ID NO 122
<211> LENGTH: 355
<212> TYPE: DNA
<213> ORGANISM: Artificial sequence
<220> FEATURE:
<223> OTHER INFORMATION: P4-141 HC nucleic acid sequence

<400> SEQUENCE: 122

```
tgaggtgcag ctggtggagt ccggggggagg cttagttcag cctggggggt ccctgagact       60
ctcctgtgca gcctccacat tcactttcaa tagctactgg atgcactggg tccgccaagc      120
tccagggaag gggctggtgt gggtgtcact tattaatcct gatggcagta ccacaaagtc      180
cgcggactcc gtgaagggcc gattcaccat ctccagagac aacgccgaga acactttgta      240
tctgcaaatg aacagtctga gagccgagga cacagctata tattactgcg ccggagctta      300
tagcagtggc tggtataaga ggtggggcca gggaaccctg gtcaccgtct cctca           355
```

<210> SEQ ID NO 123
<211> LENGTH: 321
<212> TYPE: DNA
<213> ORGANISM: Artificial sequence
<220> FEATURE:
<223> OTHER INFORMATION: P4-141 LC nucleic acid sequence

<400> SEQUENCE: 123

```
gacatccaga tgacccagtc tccatcctcc ctgtctgcat ctgtgggaga cagagtcacc       60
atctcttgcc gggcgagtca gggcattagc aggtctttag cctggtatca gcagaaacca      120
gggaaagccc ctcagctcct gctctatggt gcgtccagat tggaaagtgg ggtcccatcc      180
aggttcagtg gcactggatc tgggacggat tacactctca ccatcagcag cctgcagcct      240
gaagattttg caacttatta ctgtcaacaa tattataatg ttccctatac ttttggccag      300
gggaccaagc tggagattaa a                                                321
```

<210> SEQ ID NO 124
<211> LENGTH: 375
<212> TYPE: DNA
<213> ORGANISM: Artificial sequence
<220> FEATURE:
<223> OTHER INFORMATION: P4-163 HC nucleic acid sequence

<400> SEQUENCE: 124
gaggtgcagc tggtggagtc tggggggaggc ctggtcaagc cggggggggtc cctgagactc      60 tcctgtgcag cctctggatt caccttcgaa agccatagga tgcactgggt ccgccaggct     120
ccagggaagg ggctagaatg ggtctcatcc attattagta gtcgaactta catatactac     180
gcagactcag tgaagggccg attcaccatc tccagagaca actccaggaa ctcactcttt     240
ctacaaatga acagcctgag agccgaggac acggctgtgt attactgtgc acgaggagac     300
tactactatg atggtgttgc ctcagatcct cactttgaca ctggggccca gggaaccctg     360
gtcaccgtct cctca                                                      375

<210> SEQ ID NO 125
<211> LENGTH: 330
<212> TYPE: DNA
<213> ORGANISM: Artificial sequence
<220> FEATURE:
<223> OTHER INFORMATION: P4-163 LC nucleic acid sequence

<400> SEQUENCE: 125
cagtctgtgc tgactcagcc accctcagcg tctgggaccc ccggtcagag ggtcaccatc      60
tcttgttctg gcggcaggtc caacatcgga agtaattatg tatactggtt ccagcagctc     120
ccaggaacgg cccccccaact cctcatctat aggaatattc agcggccctc aggggtccct     180
gcccgattct ctggctccaa gtctggcacc tcagcctcac tggccatcag tgggctccgg     240
tccgaggatg aggctgatta ttactgtgca acatgggatg acagcctgag tggtgtggtt     300
ttcggcggag ggaccaaggt gaccgtccta                                      330

<210> SEQ ID NO 126
<211> LENGTH: 375
<212> TYPE: DNA
<213> ORGANISM: Artificial sequence
<220> FEATURE:
<223> OTHER INFORMATION: P4-170 HC nucleic acid sequence

<400> SEQUENCE: 126
gaggtgcagc tggtggagtc gggggggaggc ctggtcaagc cgggtgggtc cctgagactc      60
tcctgtgcag cctccggatt caccttcagt agccatagga tgcactgggt ccgccaggct     120
ccagggaagg ggctggagtg ggtctcatcc attattagta gtcgaactta tatatactac     180
gcagactcag tgaagggccg attcaccatc tccagagaca actccgggaa ctcactgttt     240
ctgcaaatga acagcctgag agtcgaggac acggctgttt attactgtgc gcgaggagac     300
tactactatg atggtgttgc ctcagaccct cactttgaca ctggggccca gggaaccctg     360
gtcaccgtct cctca                                                      375

<210> SEQ ID NO 127
<211> LENGTH: 330
<212> TYPE: DNA
<213> ORGANISM: Artificial sequence
<220> FEATURE:
<223> OTHER INFORMATION: P4-170 LC nucleic acid sequence

<400> SEQUENCE: 127

-continued cagtctgtgc tgacgcagac accctcagcg tctgggaccc ccgggcagag ggtcaccatc        60
tcttgttctg gcagcaggtc caacattgga agtaattacg tatactggtt ccagcagttc       120
ccaggagcgg cccccaact cctcatctat aggaatattc agcggccctc aggggtccct        180
gcccgattct ctggctccaa gtctgacacc tcagcctcac tggccatcag tggactccgg       240
tccgaggatg aggctcatta ttactgtgca gcatgggatg acagcctgag tggtgtggtt       300
ttcggcggag ggaccaaggt gaccgtccta                                        330

<210> SEQ ID NO 128
<211> LENGTH: 385
<212> TYPE: DNA
<213> ORGANISM: Artificial sequence
<220> FEATURE:
<223> OTHER INFORMATION: P4-36GL_HC nucleic acid sequence

<400> SEQUENCE: 128
gaggtgcagc tggtggagtc tgggggaggc ttggtacagc cagggcggtc cctgagactc        60
tcctgtacag cttctggatt cacctttggt gattatgcta tgagctgggt ccgccaggct       120
ccagggaagg ggctggagtg ggtaggtttc attagaagca aagcttatgg tgggacaaca       180
gaatacgccg cgtctgtgaa aggcagattc accatctcaa gagatgattc caaaagcatc       240
gcctatctgc aaatgaacag cctgaaaacc gaggacacag ccgtgtatta ctgtactggg       300
cctcggcctt attatgatag tagcggttat tacccgtatt attttgacta ctggggccag       360
ggaaccctgg tcaccgtctc ctcag                                             385

<210> SEQ ID NO 129
<211> LENGTH: 333
<212> TYPE: DNA
<213> ORGANISM: Artificial sequence
<220> FEATURE:
<223> OTHER INFORMATION: P4-36GL_LC nucleic acid sequence

<400> SEQUENCE: 129
cagtctgccc tgactcagcc tcgctcagtg tccgggtctc ctggacagtc agtcaccatc        60
tcctgcactg gaaccagcag tgatgttggt ggttataact atgtctcctg gtaccaacag       120
cacccaggca aagcccccaa actcatgatt tatgatgtca gtaagcggcc ctcaggggtc       180
cctgatcgct tctctggctc caagtctggc aacacggcct ccctgaccat ctctgggctc       240
caggctgagg atgaggctga ttattactgc tgctcatatg caggcagcta cacttatgtg       300
gtattcggcg gagggaccaa gctgaccgtc cta                                    333

<210> SEQ ID NO 130
<211> LENGTH: 376
<212> TYPE: DNA
<213> ORGANISM: Artificial sequence
<220> FEATURE:
<223> OTHER INFORMATION: P4-163GL_HC nucleic acid sequence

<400> SEQUENCE: 130
gaggtgcagc tggtggagtc tgggggaggc ctggtcaagc ctgggggtc cctgagactc         60 tcctgtgcag cctctggatt caccttcagt agctatagca tgaactgggt ccgccaggct       120
ccagggaagg ggctggagtg ggtctcatcc attagtagta gtagtagtta catatactac       180
gcagactcag tgaagggccg attcaccatc tccagagaca cgccaagaa ctcactgtat        240 ctgcaaatga acagcctgag agccgaggac acggctgtgt attactgtgc gagaggagac       300

-continued

```
tactactatg atggtgttgc ctcagatcct cactttgaca actggggcca gggaaccctg      360
gtcaccgtct cctcag                                                      376

<210> SEQ ID NO 131
<211> LENGTH: 330
<212> TYPE: DNA
<213> ORGANISM: Artificial sequence
<220> FEATURE:
<223> OTHER INFORMATION: P4-163GL_LC nucleic acid sequence

<400> SEQUENCE: 131
cagtctgtgc tgactcagcc accctcagcg tctgggaccc ccgggcagag ggtcaccatc       60
tcttgttctg gaagcagctc caacatcgga agtaattatg tatactggta ccagcagctc      120
ccaggaacgg cccccaaact cctcatctat aggaataatc agcggccctc aggggtccct      180
gaccgattct ctggctccaa gtctggcacc tcagcctccc tggccatcag tgggctccgg      240
tccgaggatg aggctgatta ttactgtgca gcatgggatg acagcctgag tggtgtggta      300
ttcggcggag ggaccaagct gaccgtccta                                       330
```

COMPOSITIONS AND METHODS FOR THE TREATMENT OF TUBERCULOSIS

RELATED APPLICATION(S)

This application is a National Phase of PCT Patent Application No. PCT/IL2019/050801 having International filing date of Jul. 16, 2019, the contents of which are all incorporated by reference as if fully set forth herein in their entirety.

SEQUENCE LISTING STATEMENT

The ASCII file, entitled 89596Sequence-Listing.txt, created on Jan. 14, 2022, comprising 64,280 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to compositions and methods for the treatment of Tuberculosis.

Tuberculosis ("TB"), is caused by *Mycobacterium* infection, most typically, *Mycobacterium tuberculosis* (also referred to as "MTB"), and ranks in the top three etiologies of infectious disease mortality. Drug resistant strains make this pathogen especially dangerous as both a general health hazard and a potential bioterrorism agent. Tuberculosis primarily impacts the lungs, although it can also affect other parts of the body, such as the brain, the kidneys, or the spine, and it is spread by transmission of respiratory fluids through the air (e.g., as a result of coughing or sneezing by an infected person). While many TB infections are latent (asymptomatic), approximately 10% of these latent infections eventually become active disease which, when untreated, kills more than 50% of infected patients.

Approximately one third of the world's population is thought to have been infected with MTB. Although the absolute number of TB cases has been decreasing since the early-mid 2000's, according to the Centers for Disease Control (CDC), millions around the world become sick with TB disease each year. Moreover, TB is a leading killer of people who are MTB infected. Therefore, there remains a need worldwide for preventative and therapeutic treatments for TB.

The treatment of TB is difficult and requires administration of multiple antibiotics over a long period of time (e.g., 6-9 months). Accordingly, patient compliance with the completion of treatment can be challenging. Moreover, antibiotic resistance is a problem, where multiple drug-resistant tuberculosis (MDR-TB) infections (caused by an organism that is resistant to at least isoniazid and rifampin, currently the two most potent TB drugs) continue to increase in prevalence. In addition, although rare, cases are also emerging of extensively drug-resistant TB (XDR TB), a type of MDR TB that is resistant to isoniazid and rifampin, plus any fluoroquinolone and at least one of three injectable second-line drugs (i.e., amikacin, kanamycin, or capreomycin).

Another urgent need is for new and better preventive vaccines against tuberculosis (TB). The 100-years old BCG vaccine is ineffective in preventing new infections in adults. Current vaccine design strategies are generally focused on the enhancement of cell-mediated immunity. Antibody-based approaches were previously not considered, mostly due to the paradigm that humoral immunity plays little role in the protection against intracellular pathogens, however recent research suggests that induction of antibody-mediated immunity should be included in TB vaccine development strategies. Specifically, several independent groups have shown protection and/or modification of the course of mycobacterial infection with passive transfer of monoclonal antibodies to mycobacterial antigens (reviewed in Jacqueline M. Achkar[1,]* and Arturo CasadevallCell Host Microbe. 2013 Mar. 13; 13 (3): 250-262 and references therein). Others have shown conflicting evidence to the role of antibody-mediated immunization (AMI) against TB (as reviewed in Jacobs et al. Tuberculosis (Edinb). 2016 December; 101: 102-113 and references thereon).

ADDITIONAL RELATED ART

US20170023586

Shin et al. in Clinical and Vaccine Immunology 13 (8):869-75. September 2006;

Rodríguez et al. Vaccine. 2005; 23:2565-2572;

Furuya et al. Infect Immun. 2013; 81:3434-3441.

Freund et al A New Glycan-Dependent CD4-Binding Site Neutralizing Antibody Exerts Pressure on HIV-1 In Vivo, PloS pathogens, 2015;

Freund et al, Coexistence of potent HIV-1 broadly neutralizing antibodies and antibody-sensitive viruses in a viremic controller, Science Trans Med, 9, 373, 2017;

Freund et al Amplification of highly mutated human Ig lambda light chains from an HIV-1 infected patient, J Immunol Methods, 418, 61-65, 2015.

SUMMARY OF THE INVENTION

According to an aspect of some embodiments of the present invention there is provided a human antibody comprising an antigen binding domain which binds PstS1 of *Mycobacterium tuberculosis* (TB) for use in preventing or treating TB infection in a subject in need thereof.

According to an aspect of some embodiments of the present invention there is provided a method of preventing or treating *Mycobacterium tuberculosis* (TB) infection in a subject in need thereof, the method comprising administering to the subject an effective amount of a human antibody comprising an antigen binding domain which binds PstS1, thereby preventing or treating TB in the subject.

According to an aspect of some embodiments of the present invention there is provided a method of producing an antibody capable of binding Psts1 of *Mycobacterium tuberculosis* (TB), the method comprising:

(a) expressing in a host cell a heterologous polynucleotide encoding a human antibody comprising an antigen binding domain which binds the PstS1; and optionally (b) recovering the antibody from the host cell.

According to an aspect of some embodiments of the present invention there is provided a vaccine comprising an effective amount of a human antibody comprising an antigen binding domain which binds PstS1 of *Mycobacterium tuberculosis* (TB) and an excipient.

According to an aspect of some embodiments of the present invention there is provided a human antibody comprising an antigen binding domain which binds PstS1 of *Mycobacterium tuberculosis* (TB) attached to a heterologous effector moiety or carrier.

According to some embodiments of the invention, the antibody binds the PstS-1 at a KD<5 nM.

According to some embodiments of the invention, the antibody increases macrophage uptake of both an attenuated and pathogenic TB strains.

According to some embodiments of the invention, the antibody binds a recombinant PstS1.

According to some embodiments of the invention, the antibody binds a plasma membrane of the TB.

According to some embodiments of the invention, the antibody binds both an attenuated and pathogenic TB strains.

According to some embodiments of the invention, the antibody is a recombinant antibody.

According to some embodiments of the invention, the antigen binding domain comprises the complementarity determining regions (CDRs) CDRH1, CDRH2, CDRH3, CDRL1, CDRL2 and CDRL3 or the heavy chain and light chain of an antibody selected from the group listed in Table 1.

According to some embodiments of the invention, the antigen binding domain comprises CDRH1, CDRH2, CDRH3, CDRL1, CDRL2 and CDRL3 of P4-36.

According to an aspect of some embodiments of the present invention there is provided an antibody capable of binding Psts1 of *Mycobacterium tuberculosis* (TB), the antibody comprising an antigen binding domain comprising the complementarity determining regions (CDRs) CDRH1, CDRH2, CDRH3, CDRL1, CDRL2 and CDRL3 or the heavy chain and light chain of an antibody selected from the group listed in Table 1 for use in preventing or treating TB in a subject in need thereof.

According to an aspect of some embodiments of the present invention there is provided a method of preventing or treating *Mycobacterium tuberculosis* (TB) in a subject in need thereof, the method comprising administering to the subject an effective amount of an antibody capable of binding PstS1 of TB, the antibody comprising an antigen binding domain comprising the complementarity determining regions (CDRs) CDRH1, CDRH2, CDRH3, CDRL1, CDRL2 and CDRL3 or the heavy chain and light chain of an antibody selected from the group listed in Table 1, thereby preventing or treating TB in the subject.

According to an aspect of some embodiments of the present invention there is provided a method of detecting a *Mycobacterium tuberculosis* (TB) infection, the method comprising contacting a biological sample suspected of being infected with TB with a human antibody comprising an antigen binding domain which binds PstS1 of *Mycobacterium tuberculosis* (TB) under conditions which allow a specific immunocomplex formation between the antibody and the PstS1, wherein a presence of the immunocomplex is indicative of *Mycobacterium tuberculosis* (TB) infection.

According to some embodiments of the invention, an antigen binding domain of the antibody comprises the complementarity determining regions (CDRs) CDRH1, CDRH2, CDRH3, CDRL1, CDRL2 and CDRL3 or the heavy chain and light chain of an antibody selected from the group listed in Table 1.

According to some embodiments of the invention, an antigen binding domain of the antibody comprises CDRH1, CDRH2, CDRH3, CDRL1, CDRL2 and CDRL3 of P4-36.

According to some embodiments of the invention, the antibody is labeled.

According to some embodiments of the invention, the contacting is effected in-vivo.

According to some embodiments of the invention, the contacting is effected ex-vivo.

According to an aspect of some embodiments of the present invention there is provided a diagnostic kit for detecting a *Mycobacterium tuberculosis* (TB) infection, the kit comprising a human antibody comprising an antigen binding domain which binds PstS1 of *Mycobacterium tuberculosis* (TB) which allow a specific immunocomplex formation between the antibody and the PstS1.

According to some embodiments of the invention, an antigen binding domain of the antibody comprises the complementarity determining regions (CDRs) CDRH1, CDRH2, CDRH3, CDRL1, CDRL2 and CDRL3 or the heavy chain and light chain of an antibody selected from the group listed in Table 1.

According to some embodiments of the invention, an antigen binding domain of the antibody comprises CDRH1, CDRH2, CDRH3, CDRL1, CDRL2 and CDRL3 of P4-36.

According to some embodiments of the invention, the antibody is labeled.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-H show results of ELISA experiments with Israeli cohort sera per patient. (FIGS. 1A-E) The plates were coated with 5 ug/ml of recombinant antigens overnight at 4 C. On the next day the plates were washed and blocked for 2 hours with PBS 2% BSA 0.5 mM EDTA, subsequently incubated with sera in 1:300 dilution from actively infected (black), or community controls (grey). The different donors are indicated in symbols at the lower right panel of the figure. The results were analyzed using One-way ANOVA. (FIG. 1F) The heat map summarizes the responders and the antigens they bound. (FIGS. G-H) patients' and healthy donors' sera response to H37Ra cell lysate and Cell wall components. Symbols and statistical analysis is same as in (FIGS. 1A-E).

FIGS. 2A-D Antibody isolation from patient 004. (FIG. 2A) Flow cytometry and gating strategy of ficoll-isolated PBMCs preincubated with CD20 magnetic beads. From left to right: lymphocytes were identified, then we gated on IgG+ B cells, from which the PstS1 positive B cells were single cell sorted as indicated. (FIG. 2B) Pie charts depict the Vh sequences of the single cell sorted PstS1+IgG+ B cells that were subjected in (A). Left panel: a total of 108 Vh sequences obtained, of which the light gray slice represents sequences that appeared only once and the smaller black and white slices represents clonal sequences. Right panel: the pie chart depicts only the five clonally related family of sequences (FIG. 2C) Nucleotide mutation analysis of the clonal versus non-clonal Vh sequences. (FIG. 2D) the total Vh gene distribution of the sequences as obtained by alignment to IgGBlast and sequence analysis.

FIGS. 3A-C show characteristics of monoclonal Antibodies isolated from Patient 004. (FIG. 3A) ELISA of five antibodies P4-163, P4-170, P4-141, P4-36 and P4-31 cloned from single B cells of Patient 004 and reacted against PstS1 (left panel) or MBP (right panel). MGO53 is an IgG1 antibody isolated from a healthy donor and BG18 is an anti-HIV-1 antibody isolated from patient EB354 (Freund et al Science Tras Med. 2017). (FIG. 3B) Flow cytometry of H37ra Mtb strain stained with the five antibodies P4-163, P4-170, P4-141, P4-36 and P4-31 cloned from single B cells of Patient 004 as well as MGO53 control. A quantification of the experiment is shown on the bottom left panel. (FIG. 3C) Confocal microscopy showing binding of P4-36 mAb to the pathogenic MTB strain Erdman.

FIG. 4 shows Mtb uptake by macrophages. Human macrophages were infected with H37Ra and following three hours of infection the cells were thoroughly washed with PBS and incubated with Akinomycin for an hour to remove all extracellular bacteria. Next, the cells were washed again and lysed and the intracellular bacteria were plated on solid agar plates and incubated in 37 C for three weeks. The numbers represent the number of colonies counted in 10E-2 dilution.

DESCRIPTION OF SPECIFIC EMBODIMENTS OF THE INVENTION

The present invention, in some embodiments thereof, relates to compositions and methods for the treatment of Tuberculosis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Monoclonal antibodies have proven extremely efficacious and safe immunodrugs for the treatment of various diseases, such as cancer and autoimmune disorders (e.g., Rheumatic Arthritis).

The use of passive immunization in the treatment of *Mycobacterium tuberculosis* (TB) is controversial with evidence supporting it and contradicting it spread throughout the scientific literature. However, to date, no one has suggested isolating naturally occurring anti TB antibodies from infected human subjects for use in passive immunity.

Using single B cell sorting, the present inventors have now isolated monoclonal antibodies against the PstS1 protein of MTB from an infected donor. PstS1 is a *Mycobacterium tuberculosis* membrane embedded ABC transporter, also acting as a virulence factor. The new monoclonal antibodies bind PstS1 with an exceptional affinity (pM range) and bind both the attenuated and the pathogenic *Mycobacterium tuberculosis* strains. Thus, these antibodies hold a massive therapeutic potential and can be used also and in diagnostic kits.

Thus, according to an aspect of the invention there is provided a human antibody comprising an antigen binding domain which binds PstS1 of *Mycobacterium tuberculosis* (TB) for use in preventing or treating TB infection in a subject in need thereof.

Alternatively or additionally there is provided a method of preventing or treating *Mycobacterium tuberculosis* (TB) infection in a subject in need thereof, the method comprising administering to the subject an effective amount of a human antibody comprising an antigen binding domain which binds PstS1, thereby preventing or treating TB in the subject.

Alternatively or additionally there is provided an antibody capable of binding PstS1 of MTB, the antibody comprising an antigen binding domain comprising the complementarity determining regions (CDRs) CDRH1, CDRH2, CDRH3, CDRL1, CDRL2 and CDRL3 or the heavy chain and light chain of an antibody selected from the group listed in Table 1 for use in preventing or treating TB in a subject in need thereof When referring to the antibodies in Table 1 the meaning is for heavy chain and light chain of a specific antibody e.g., P4-163 (SEQ IDs 17-24), P4-170 (SEQ IDs 33-40), from clone 2: P4-141 (SEQ IDs 57-64), from clone 3: P4-36 (SEQ ID 81-88), from clone 4: P4-31 (SEQ ID 89-96) or any other antibody listed in the Table.

Alternatively or additionally there is provided a method of preventing or treating MTB in a subject in need thereof, the method comprising administering to the subject an effective amount of an antibody capable of binding PstS1 of MTB, the antibody comprising an antigen binding domain comprising the complementarity determining regions (CDRs) CDRH1, CDRH2, CDRH3, CDRL1, CDRL2 and CDRL3 or the heavy chain and light chain of an antibody selected from the group listed in Table 1, thereby preventing or treating TB in the subject.

As used herein "MTB infection" refers to a species of pathogenic bacteria in the family Mycobacteriaceae and the causative agent of tuberculosis, a disease caused by an infection by the bacteria. Symptoms of the disease are listed below in a non-limiting manner. Differential diagnosis of TB is possible such as following the guidelines provided in www(dot)wikidoc(dot)org/index(dot)php/Tuberculosis_differential_diagnosis.

The present teachings relate to preventive (prophylactic) and therapeutic aspects.

As used herein "subject" refers to a human or non-human (animal) subject such as mammals such as rats, mice, rabbits, sheep, cats, dogs, cows, pigs, and non-human primates. The subject may be infected with MTB, exposed to MTB, or being at risk of exposure to MTB.

The subject may have a latent or active infection by a virulent strain of MTb.

The strain may be multi-drug resistant (MDR) or extensively drug resistant (XDR) to traditional therapies/antibiotics.

As used herein, the term "treating" refers to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder associated with TB infection. Treatment is generally "effective" if one or more symptoms or clinical markers are reduced. Alternatively, treatment is "effective" if the progression of a disorder is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of the disorder, stabilized (i.e., not worsening) state of the disorder, delay or slowing of disorder progression, amelioration or palliation of the disorder state, and remission (whether partial or total), whether detectable or undetectable. The term "treatment" of a disorder also includes providing relief from the symptoms or side-effects of the disorder (including palliative treatment).

According to a specific embodiment "treating" refers to treatment of active TB disease i.e., when MTB actively replicates and causes direct damage. The antibody of some aspects of the invention can be used alone or as part of a combined treatment with other modalities of treatment against TB.

According to a specific embodiment "preventing reactivation" refers to keeping MTB in a latent/dormant stage and preventing reactivation of MTB, i.e maintaining the bacteria in its latent/dormant stage, where it is not actively replicating and causing direct damage.

As used herein "preventing infection" refers to prevention of MTB infection in a subject who is uninfected by MTB (does not have a dormant/latent MTB in the body). Some non-limiting risk factors are listed below.

Prevention can be done by means of immunization, in this case passive immunization, where the antibody is administered.

Subjects having TB infection or suffering from the symptoms of TB infection can be identified by a physician using current methods of diagnosing TB infections or as further described hereinbelow. Symptoms and/or complications of TB infection useful in making such diagnoses include, but are not limited to chronic cough, blood-tinged sputum, fever, chest pain, pallor, chills, fatigue, night sweats, and weight loss. If TB infection spreads to organs other than the lungs, a variety of symptoms can arise that are specific to the particular organ infected. Test and diagnostic tools that may aid in a diagnosis of TB infection include, but are not limited to x-rays, chest x-rays, tuberculin skin test, blood tests, microscopic examination of bodily fluids, microbiological culture of bodily fluids, chest photofluorography, the Ziehl-Neelsen stain, auramine-rhodamine stain, fluorescent microscopy, PCR tests, amplified *Mycobacterium tuberculosis* direct test (MTD, Gen-Probe) or an interferon gamma release assay (IGRA).

Subjects can have an elevated risk of having or developing a TB infection for a number of reasons. Risk factors that predispose a subject to TB include, but are not limited to, certain polymorphisms in the IL12B gene, a family history of TB infection, treatment with immunosuppressive drugs, treatment for rheumatoid arthritis with anti-TNF alpha therapy, illegal drug use, low BMI, AIDS, silicosis, exposure to silica particles, diabetes mellitus, jejunoileal bypass, renal and cardiac transplantation, carcinoma of the head or neck, other neoplasms, terror attacks and incarceration in a prison.

MTB infects macrophages using a variety of microbial ligand/cell receptor systems. Binding assays with biotin-labelled mycobacterial cell wall proteins revealed five Con-canavalin A-reactive proteins that bind macrophages. Among these proteins, PstS1, a 38-kDa *M. tuberculosis* mannosylated glycolipoprotein, also known as adhesin, plays a major role. Inhibition assays with mannan and immunoprecipitation demonstrated that PstS1 binds the mannose receptor (Esparza et al. *Scand J Immunol.* 2015 January; 81 (1):46-55).

As used herein "PstS1" or "PstS-1" or "Phosphate-binding protein PstS1" refers to the protein product of GeneID 885724.

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen, in this case PstS1.

According to specific embodiments, the antibody is a whole or intact antibody.

According to specific embodiments, the antibody is an antibody fragment.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDRH1 or H1; CDRH2 or H2; and CDRH3 or H3) and three in each of the VL (CDRL1 or L1; CDRL2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

According to specific embodiments the antibody heavy chain constant region is chosen from, e.g., IgG1, IgG2, IgG3, IgG4, IgM, IgA1, IgA2, IgD, and IgE.

According to specific embodiments, the antibody is an IgG antibody.

According to a specific embodiment the antibody isotype is IgG1 or IgG4.

The choice of antibody type will depend on the immune effector function that the antibody is designed to elicit.

According to specific embodiments, the antibody comprises an Fc domain.

According to specific embodiments, the antibody is a naked antibody.

As used herein, the term "naked antibody" refers to an antibody which does not comprise a heterologous effector moiety e.g. therapeutic moiety, detectable moiety.

As used herein "heterologous" means not occurring in nature in conjunction with the antibody.

According to specific embodiments, the antibody comprises a heterologous effector moiety e.g. e.g. therapeutic moiety, detectable moiety. The effector moiety can be proteinaceous or non-proteinaceous; the latter generally being generated using functional groups on the antibody and on the conjugate partner. The effector moiety may be any molecule, including small molecule chemical compounds and polypeptides. For example the effector moiety can be a known drug to TB infection.

According to specific embodiments, the antibody is a monoclonal antibody.

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

It will be appreciated that for human therapy or diagnostics, humanized antibodies are preferably used.

According to specific embodiments, the antibody is a humanized antibody. Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

According to preferred embodiments, the antibody is a human antibody.

According to a specific embodiment, the human antibody carries human Vh, Dh, Jh, Vl, J, gene segments such as in germ line antibodies or natural variants thereof. Although synthetic antibodies are also contemplated.

According to a specific embodiment, the antibody is a homolog of a human antibody comprising a sequence at least 90% identical to VH chain 3-21, 3-49, 1-46, 3-74 or 3-11.

According to a specific embodiment, when the VH chain is at least 90% identical to 3-49, the VL chain is at least 90% identical to L2-11; or when the VH chain is at least 90% identical to 3-21, the VL chain is at least 90% identical to L1-47;

when the VH chain is at least 90% identical to 1-46, the VL chain is at least 90% identical to L3-25.

As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89 (22): 10915-9].

Identity (e.g., percent homology) can be determined using any homology comparison software, including for example, the BlastN or BlastP software of the National Center of Biotechnology Information (NCBI) such as by using default parameters.

When referring to "at least 90% identity" the claimed invention also refer to at least 91%, at least 92%, at least 93%, at least 94%, at least 95%, at least 96%, at least 97%, at least 98%, at least 98% or 100% identity where each represents a different embodiment.

According to a specific embodiment, the antibody is a homolog of a human antibody comprising a sequence at least 90% identical to VH chain 3-21 (SEQ ID NO: 1, SEQ ID NO:9, SEQ ID NO:17, SEQ ID NO:25, SEQ ID NO:33, SEQ ID NO:41, SEQ ID NO: 49), 3-49 (SEQ ID NO: 73, SEQ ID NO: 81), 1-46 (SEQ ID NO: 89, 97), 3-74 (SEQ ID NO: 57, 65, 69) or 3-11 (SEQ ID NO: 101, 105).

According to a specific embodiment, the level of identity is at least 90% over the entire sequence (any of the VH and/or VL chains described herein including germ line chains e.g., 3-74, 3-21, L1-47, K1-NL1, 3-49, L2-11, 1-46, L3-25, 3-11) such as determined as described herein.

According to a specific embodiment, the level of identity is at least 90% over the entire sequence (any of the VH and/or VL chains described herein including germ line chains e.g., 3-74, 3-21, L1-47, K1-NL1, 3-49, L2-11, 1-46, L3-25, 3-11) such as determined as described herein.

According to a specific embodiment, the level of identity is at least 90% over the entire sequence (any of the VH and/or VL chains described herein including germ line chains e.g., 3-74, 3-21, L1-47, K1-NL1, 3-49, L2-11, 1-46, L3-25, 3-11) such as determined as described herein.

According to a specific embodiment, the level of identity is at least 90% over the entire sequence (any of the VH and/or VL chains described herein including germ line chains e.g., 3-74, 3-21, L1-47, K1-NL1, 3-49, L2-11, 1-46, L3-25, 3-11) such as determined as described herein. According to a specific embodiment, the level of identity is at least 96% over the entire sequence (VH and/or VL) such as determined as described herein.

According to a specific embodiment, the level of identity is at least 90% over the entire sequence (any of the VH and/or VL chains described herein including germ line chains e.g., 3-74, 3-21, L1-47, K1-NL1, 3-49, L2-11, 1-46, L3-25, 3-11) such as determined as described herein.

According to a specific embodiment, the level of identity is at least 90% over the entire sequence (any of the VH and/or VL chains described herein including germ line chains e.g., 3-74, 3-21, L1-47, K1-NL1, 3-49, L2-11, 1-46, L3-25, 3-11) such as determined as described herein.

According to a specific embodiment, the level of identity is at least 90% over the entire sequence (any of the VH and/or VL chains described herein including germ line chains e.g., 3-74, 3-21, L1-47, K1-NL1, 3-49, L2-11, 1-46, L3-25, 3-11) such as determined as described herein.

Exemplary CDR sequences and complete light and heavy chains of human antibodies are provided in Table 1 below (which is a duplicate of Table 2 below).

TABLE 1 complete amino acid sequences and CDR sequences of antibodies
of some embodiments of the invention (the CDR sequences
determined according to the Kabat system)

| Clone | Name | SEQ ID NO: | Sequence |
|---|---|---|---|
| 1 | P4-110 IgH | 1 | EVQLVQSGGGLVKPGGSLRLSCAASGFTFSRHTMHWVRLAPGK GLEWVSSILSSPTYIYYADSVKGRFTISRDNSGNSLFLQMNSLRVD DTAVYYCARGDYYYDGVASDPHFDNWGQGTLVTVSS |
| 1 | CDRH1 | 2 | GFTFSRHT |
| 1 | CDRH2 | 3 | ILSSPTYI |
| 1 | CDRH3 | 4 | ARGDYYYDGVASDPHFDN |
| 1 | P4-110 IgL | 5 | QSVLTQTPSASGTPGQRVTISCSGSRSNIGSNYVYWFQQFPGAAP QLLISRNIQRPSGVPARFSGSKSDTSASLAISGLRSEDEAHYYCAA WDDSLSGVVFGGGTKVTVL |
| 1 | CDRL1 | 6 | RSNIGSNY |
| 1 | CDRL2 | 7 | RNI |
| 1 | CDRL3 | 8 | AAWDDSLSGVV |
| 1 | P4-143 IgH | 9 | EVQLVESGGGLVKPGGSLRLSCAASGFTFESHRMHWVRQAPGK GLEWVSSIISSRTYIYYADSVKGRFTISRDNSRNSLFLQMNSLRAE DTAVYYCARGDYYYDGVASDPHFDNWGQGTLVTVSS |
| 1 | CDRH1 | 10 | GFTFESHR |
| 1 | CDRH2 | 11 | IISSRTYI |
| 1 | CDRH3 | 12 | ARGDYYYDGVASDPHFDN |
| 1 | P4-143 IgL | 13 | SNYVYWFQQLPGTAPQLLIYRNIQRPSGVPARFSGSKSGTSASLAI SGLRSEDEADYYCATWDDSLSGVVFGGGTKVTVL |
| 1 | CDRL1 | 14 | SNIGSNY |
| 1 | CDRL2 | 15 | RNI |
| 1 | CDRL3 | 16 | ATWDDSLSGVV |
| 1 | P4-163 IgH | 17 | EVQLVESGGGLVKPGGSLRLSCAASGFTFESHRMHWVRQAPGK GLEWVSSIISSRTYIYYADSVKGRFTISRDNSRNSLFLQMNSLRAE DTAVYYCARGDYYYDGVASDPHFDNWGQGTLVTVSS |
| 1 | CDRH1 | 18 | GFTFESHR |
| 1 | CDRH2 | 19 | IISSRTYI |
| 1 | CDRH3 | 20 | ARGDYYYDGVASDPHFDN |
| 1 | P4-163 IgL | 21 | QSVLTQPPSASGTPGQRVTISCSGGRSNIGSNYVYWFQQLPGTAP QLLIYRNIQRPSGVPARFSGSKSGTSASLAISGLRSEDEADYYCAT WDDSLSGVVFGGGTKVTVL |
| 1 | CDRL1 | 22 | RSNIGSNY |
| 1 | CDRL2 | 23 | RNI |
| 1 | CDRL3 | 24 | ATWDDSLSGVV |
| 1 | P4-123 IgH | 25 | EVQLVESGGGLVKPGGSLRLSCAASGFTFESHRMHWVRQAPGK GLEWVSSIISSRTYIYYADSVKGRFTISRDNSRNSLFLQMNSLRAE DTAVYYCARGDYYYDGVASDPHFDNWGQGTLVTVSS |
| 1 | CDRH1 | 26 | GFTFESHR |
| 1 | CDRH2 | 27 | IISSRTYI |
| 1 | CDRH3 | 28 | ARGDYYYDGVASDPHFDN |
| 1 | P4-123 IgL | 29 | QSVLTQPPSASGTPGQRVTISCSGGRSNIGSNYVYWFQQLPGTAP QLLIYRNIQRPSGVPARFSGSKSGTSASLAISGLRSEDEADYYCAT WDDSLSGVVFGGGTKVTVL |

TABLE 1-continued complete amino acid sequences and CDR sequences of antibodies
of some embodiments of the invention (the CDR sequences
determined according to the Kabat system)

| Clone | Name | SEQ ID NO: | Sequence |
|-------|------|-----------|----------|
| 1 | CDRL1 | 30 | RSNIGSNY |
| 1 | CDRL2 | 31 | RNI |
| 1 | CDRL3 | 32 | ATWDDSLSGVV |
| 1 | P4-170 IgH | 33 | EVQLVESGGGLVKPGGSLRLSCAASGFTFSSHRMHWVRQAPGK GLEWVSSIISSRTYIYYADSVKGRFTISRDNSGNSLFLQMNSLRVE DTAVYYCARGDYYYDGVASDPHFDNWGQGTLVTVSS |
| 1 | CDRH1 | 34 | GFTFSSHR |
| 1 | CDRH2 | 35 | IISSRTYI |
| 1 | CDRH3 | 36 | ARGDYYYDGVASDPHFDN |
| 1 | P4-170 IgL | 37 | QSVLTQTPSASGTPGQRVTISCSGSRSNIGSNYVYWFQQFPGAAP QLLIYRNIQRPSGVPARFSGSKSDTSASLAISGLRSEDEAHYYCAA WDDSLSGVVFGGGTKVTVL |
| 1 | CDRL1 | 38 | RSNIGSNY |
| 1 | CDRL2 | 39 | RNI |
| 1 | CDRL3 | 40 | AAWDDSLSGVV |
| 1 | P4-66 IgH | 41 | EVQLVESGGGLVKPGGSLRLSCAASGFTFSSHRMHWVRQAPGK GLEWVSSIISSRTYIYYADSVKGRFTISRDNSGNSLFLQMNSLRVE DTAVYYCARGDYYYDGVASDPHFDNWGQGTLVTVSS |
| 1 | CDRH1 | 42 | GFTFSSHR |
| 1 | CDRH2 | 43 | IISSRTYI |
| 1 | CDRH3 | 44 | ARGDYYYDGVASDPHFDN |
| 1 | P4-66 IgL | 45 | QSVLTQTPSASGTPGQRVTISCSGSRSNIGSNYVYWFQQFPGAAP QLLIYRNIQRPSGVPARFSGSKSDTSASLAISGLRSEDEAHYYCAA WDDSLSGVVFGGGTKVTVL |
| 1 | CDRL1 | 46 | RSNIGS |
| 1 | CDRL2 | 47 | RNI |
| 1 | CDRL3 | 48 | AAWDDSLSGVV |
| 1 | P4-9 IgH | 49 | EVQLVESGGGLVKPGGSLRLSCAASGFTFSSHRMHWVRQAPGK GLEWVSSIISSRTYIYYADSVKGRFTISRDDSRNSLFLQMNSLRAE DTAVYYCARGDYYYDGVASDPHFDNWGQGTLVTVSS |
| 1 | CDRH1 | 50 | GFTFSSHR |
| 1 | CDRH2 | 51 | IISSRTYI |
| 1 | CDRH3 | 52 | ARGDYYYDGVASDPHFDN |
| 1 | P4-9 IgL | 53 | QSVLTQPPSASGTPGQRVTISCSGSRSNIGSNYVYWFQQLPGTAP QLLIYRNIQRPSGVPARFSGSKSGTSASLAISGLRSEDEADYYCAA WDDSLSGVVFGGGTKVTVL |
| 1 | CDRL1 | 54 | RSNIGSNY |
| 1 | CDRL2 | 55 | RNI |
| 1 | CDRL3 | 56 | AAWDDSLSGVV |
| 2 | P4-141 IgH | 57 | EVQLVESGGGLVQPGGSLRLSCAASTFTFNSYWMHWVRQAPGK GLVWVSLINPDGSTTKSADSVKGRFTISRDNAENTLYLQMNSLR AEDTAIYYCAGAYSSGWYKRWGQGTLVTVSS |
| 2 | CDRH1 | 58 | TFTFNSYW |

TABLE 1-continued complete amino acid sequences and CDR sequences of antibodies
of some embodiments of the invention (the CDR sequences
determined according to the Kabat system)

| Clone | Name | SEQ ID NO: | Sequence |
|---|---|---|---|
| 2 | CDRH2 | 59 | INPDGSTT |
| 2 | CDRH3 | 60 | AGAYSSGWYKR |
| 2 | P4-141 IgL | 61 | DIQMTQSPSSLSASVGDRVTISCRASQGISRSLAWYQQKPGKAPQ LLLYGASRLESGVPSRFSGTGSGTDYTLTISSLQPEDFATYYCQQY YNVPYTFGQGTKLEIK |
| 2 | CDRL1 | 62 | QGISRS |
| 2 | CDRL2 | 63 | GAS |
| 2 | CDRL3 | 64 | QQYYNVPYT |
| 2 | P4-48 IgH | 65 | EVQLVQSGGGLVQPGGSLRLSCAASTFTFSSYWMHWVRQAPGK GLVWVSLINPDGSTTKSADSVKGRFTISRDNAENTLYLQMNSLR ADDTAIYYCAGAYSSGWYKRWGQGTLVAVSS |
| 2 | CDRH1 | 66 | TFTFSSYW |
| 2 | CDRH2 | 67 | INPDGSTT |
| 2 | CDRH3 | 68 | AGAYSSGWYKR |
| 2 | P4-85 IgH | 69 | EVQLVQSGGGLVQPGGSLRLSCAASTFTFSSYWMHWVRQAPGK GLVWVSLINPDGSTTKSADSVKGRFTISRDNAENTLYLQMNSLR AEDTAIYYCAGAYSSGWYKRWGQGTLVAVSS |
| 2 | CDRH1 | 70 | INPDGSTT |
| 2 | CDRH2 | 71 | TFTFSSYW |
| 2 | CDRH3 | 72 | AGAYSSGWYKR |
| 3 | P4-107 IgH | 73 | EVQLVESGGGLVQPGRSLRLSCTDSGFTFSEYALSWVRQAPGKG LEWVGFIRSKAYGGTTEYAASVKGRFTISRDDSKSVAYLQMNSL KTEDTAVYFCTGPRPYYDSSGYYPYYFDYWGQGTLVTVSS |
| 3 | CDRH1 | 74 | GFTFSEYA |
| 3 | CDRH2 | 75 | IRSKAYGGTT |
| 3 | CDRH3 | 76 | TGPRPYYDSSGYYPYYFDY |
| 3 | P4-107 IgL | 77 | QSALTQPRSVSGSPGQSVTISCTGSRSDVGGYDYVSWYQQHPGR VPKLMIYDVTKRPSGVPDRFSGSRSGNTASLTISGLQADDEADYY CSSFAGSSTYVVFGGGTTLTVL |
| 3 | CDRL1 | 78 | RSDVGGYDY |
| 3 | CDRL2 | 79 | DVT |
| 3 | CDRL3 | 80 | SSFAGSSTYVV |
| 3 | P4-36 IgH | 81 | EVQLVESGGGLVQPGRSLRLSCTDSGFTFSEYALSWVRQAPGKG LEWVGFIRSKAYGGTTEYAASVKGRFTISRDDSKSVAYLQMNSL KTEDTAVYFCTGPRPYYDSSGYYPYYFDYWGQGTLVTVSS |
| 3 | CDRH1 | 82 | GFTFSEYA |
| 3 | CDRH2 | 83 | IRSKAYGGTT |
| 3 | CDRH3 | 84 | TGPRPYYDSSGYYPYYFDY |
| 3 | P4-36 IgL | 85 | QSALTQPRSVSGSPGQSVTISCTGSRSDVGGYDYVSWYQQHPGR VPKLMIYDVTKRPSGVPDRFSGSRSGNTASLTISGLQADDEADYY CSSFAGSSTYVVFGGGTTLTVL |
| 3 | CDRL1 | 86 | RSDVGGYDY |
| 3 | CDRL2 | 87 | DVT |

TABLE 1-continued complete amino acid sequences and CDR sequences of antibodies
of some embodiments of the invention (the CDR sequences
determined according to the Kabat system)

| Clone | Name | SEQ ID NO: | Sequence |
|---|---|---|---|
| 3 | CDRL3 | 88 | SSFAGSSTYVV |
| 4 | P4-31 IgH | 89 | QVQLVQSGAEVKNPGASVKIACVASGHNFSDFYFHWVRQAPGQ GLEWMGIVKGGGGVTGYPQRLKGRVTMTTDTSTRTIYLELKNLT SDDTATYYCARDPGCNGGSCYYFDHWGRGTLVT |
| 4 | CDRH1 | 90 | GHNFSDFY |
| 4 | CDRH2 | 91 | VKGGGGVT |
| 4 | CDRH3 | 92 | ARDPGCNGGSCYYFDH |
| 4 | P4-31 IgL | 93 | SYELTQSTSMSVSPGQTATITCSGDALPKQYAYWYQQKSGQAPT LLIYKDNQRSSGIPDRFSGSSSGTTLTLTISGVQTEDEAVYHCQSS DITSRFVIFGGGTKLTVL |
| 4 | CDRL1 | 94 | ALPKQY |
| 4 | CDRL2 | 95 | KDN |
| 4 | CDRL3 | 96 | QSSDITSRFVI |
| 4 | P4-62 IgH | 97 | VQLVQSGAEVKKPGASLRLACTASGYNFSDFYIHWVRQAPGQG LEWMGIVKGGGGVTGYPQALRSRVTMTTDTSTTTVYMELKNISS EDTAIYYCARDPGCNGGSCYYFDHWGRGTLVTVSS |
| 4 | CDRH1 | 98 | GYNFSDFY |
| 4 | CDRH2 | 99 | VKGGGGVT |
| 4 | CDRH3 | 100 | ARDPGCNGGSCYYFDH |
| 5 | P4-13 IgH | 101 | VQLVQSGGGLVKPGGSLRLSCAASGFTFSDYYMSWIRQAPGKGL EWVSYISSSGGTVYYADSVKGRFTISRDNANNALYLQMNSLRAE DTAVYFCARDLDSASWSGYYYYYSMYVWGQGTTVTVSS |
| 5 | CDRH1 | 102 | GFTFSDYY |
| 5 | CDRH2 | 103 | ISSSGGTV |
| 5 | CDRH3 | 104 | ARDLDSASWSGYYYYYSMYV |
| 5 | P4-67 IgH | 105 | VQLVQSGGGLVKPGGSLRLSCAASGFTFSDYYMSWIRQAPGKGQ EWVSYISSSGGTVYYADSGKGRFTISRDNANNGQYQQMNSERAE DTAVYFCARDVDSASWSGYYYYYSMYVWGQGTTVTVSS |
| 5 | CDRH1 | 106 | GFTFSDYY |
| 5 | CDRH2 | 107 | ISSSGGTV |
| 5 | CDRH3 | 108 | ARDVDSASWSGYYYYYSMYV |

According to a specific embodiment, the antigen binding domain comprises CDRH1, CDRH2, CDRH3, CDRL1, CDRL2 and CDRL3 of P4-36.

Alternatively or additionally, the antibody comprises SEQ ID Nos: 81 and 85 as the heavy and light chains respectively.

Antibody P4-107 has closely related (99%) heavy chain and identical light chain sequences to P4-36 and is also contemplated according to a specific embodiment.

According to an aspect of the invention there is provided a method of producing an antibody capable of binding Psts1 of *Mycobacterium tuberculosis* (MTB), the method comprising:

(a) expressing in a host cell a heterologous polynucleotide encoding a human antibody comprising an antigen binding domain which binds the PstS1; and optionally (b) recovering the antibody from the host cell.

Thus, a polynucleotide encoding an antibody of some embodiments of the invention is cloned into an expression construct selected according to the expression system used. Exemplary polynucleotide sequences are provided in SEQ ID NOs: 109-131.

A variety of prokaryotic or eukaryotic cells can be used as host-expression systems to express the antibody of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the antibodies of some embodiments of the invention.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMT010/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Examples of bacterial constructs include the pET series of *E. coli* expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by some embodiments of the invention.

It will be appreciated that antibodies can also be produced in in-vivo systems such as in mammals, e.g., goats, rabbits etc.

Recovery of the recombinant antibody is effected following an appropriate time (in culture). The phrase "recovering the antibody" refers to collecting the whole fermentation medium containing the antibody and need not imply additional steps of separation or purification. Notwithstanding the above, antibodies of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Once antibodies are obtained, they may be tested for activity.

According to some embodiments, the antibody comprises an antigen binding domain which binds PstS1 of TB at a $K_D$<5 nM.

According to a specific embodiment, the antibody comprises an antigen binding domain which binds PstS1 of TB at a $K_D$<2 nM.

Antibody comprises an antigen binding domain which binds PstS1 of TB at a $K_D$<1 nM.

As used herein "binding" or "binds" refers to an antibody-antigen mode of binding, which is generally, in the range of $K_D$ below 1 nM, as determined by ELISA using the recombinant PstS-1 protein.

According to another specific embodiment, the affinity of the antibody to its antigen is determined by Surface Plasmon Resonance (SPR).

As used herein the term "$K_D$" refers to the equilibrium dissociation constant between the antigen binding domain and its respective antigen.

According to a specific embodiment, the antibody comprises an antigen binding domain which binds PstS1 of TB at a $K_D$ 50 pM-5 nM.

According to a specific embodiment, the antibody comprises an antigen binding domain which binds PstS1 of TB at a $K_D$ 50 pM-2 nM.

According to a specific embodiment, the antibody comprises an antigen binding domain which binds PstS1 of TB at a $K_D$ 50 pM-1 nM.

According to a specific embodiment, the antibody comprises an antigen binding domain which binds PstS1 of TB at a $K_D$ 50 pM-500 pM.

According to a specific embodiment, the antibody comprises an antigen binding domain which binds PstS1 of TB at a $K_D$ 100 pM-5 nM.

According to a specific embodiment, the antibody comprises an antigen binding domain which binds PstS1 of TB at a $K_D$ 100 pM-2 nM. According to a specific embodiment, the antibody comprises an antigen binding domain which binds PstS1 of TB at a $K_D$ 100 pM-1 nM.

According to a specific embodiment, the antibody comprises an antigen binding domain which binds PstS1 of TB at a $K_D$ 100 pM-500 pM. As mentioned, the antibody of some embodiments of the invention the antibody increases macrophage uptake of both an attenuated and pathogenic TB strains.

As used herein "increase" refers to an elevation of at least 10% (statistically significant increase), 20%, 30%, 50%, 60%, 70%, 80%, 90% or more e.g., at least 2 fold, 3 fold, 5 fold or 10 fold, in macrophage uptake of the bacteria in the presence of the antibody as compared to its absence but otherwise using the same assay conditions, also referred to as "control". This uptake inhibits bacterial growth inside the macrophage by a mechanism which is yet not discovered. According to a specific embodiment, the antibody e.g., mAb P4-36, inhibits MTB growth both ex-vivo in whole blood assay and in vivo in MTB infected mice.

As shown in the Examples section which follows, antibodies of some embodiments of the invention bind a recombinant PstS1 that is produced in *E. coli* (i.e., a protein that is produced by recombinant DNA technology means and does not necessarily share the same post translational modifications as the natural protein in the bacteria).

Alternatively or additionally, according to some embodiments of the invention, the antibody binds a plasma membrane of the TB, via said PstS-1, namely in its natural environment as determined by confocal microscopy.

Alternatively or additionally, the antibody binds both an attenuated and pathogenic TB strains. As shown in the Examples section which follows, the antibody binds the pathogenic TB Erdman strain and the attenuated H37Ra strain, as determined by confocal microscopy and FACS, respectively.

The antibody may be soluble or non-soluble.

Non-soluble antibodies may be a part of a particle (synthetic or non-synthetic, e.g., liposome) or a cell (e.g., CAR-T cells).

Increasing the cytotoxic activity of an antibody where necessary can also be achieved such as by using an antibody-drug conjugate (ADC) concept. In such a configuration the antibody is attached to a heterologous effector moiety that can be used to increase its toxicity or to render it detectable.

In a whole antibody, a therapeutic activity is intrinsic to the molecule since the Fc domain activates antibody-dependent cell-mediated cytotoxicity (ADCC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. For example, eosinophils can kill certain parasitic worms known as helminths through ADCC mediated by IgE. ADCC is part of the adaptive immune response due to its dependence on a prior antibody response.

Alternatively or additionally and as mentioned, the antibody may be a bispecific antibody in which the therapeutic moiety is a T cell engager for example, such as an anti CD3 antibody or an anti CD16a.

Alternatively or additionally the antibody may be attached to a heterologous therapeutic moiety (methods of conjugation are known in the art). The therapeutic moiety can be, for example, a cytotoxic moiety, a toxic moiety, a cytokine moiety, a drug. Examples include, but are not limited to toxins e.g., purothionin, pseudomonas exotoxin A, methotrexate.

Thus, the antibody of some embodiments of the present invention may find therapeutic or prophylactic uses such as a vaccine.

Thus, according to an aspect of the invention there is provided a vaccine comprising an effective amount of a human antibody comprising an antigen binding domain which binds PstS1 of *Mycobacterium tuberculosis* (TB) at a $K_D < 1$ nM and an excipient.

According to a specific embodiment, the vaccine comprises the CDRs of an antibody listed in Table 1 above, or the corresponding heavy chains and light chains.

According to a specific embodiment, the protein fraction of the vaccine comprises at least 50%, or 60%, or 70% or 80% or 90% or 95% or 98% or 99% the antibody of some embodiments of the invention.

For therapeutic treatments the antibody can be provided to the subject per se or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Pharmaceutical compositions or vaccines suitable for use in context of some embodiments of the invention include compositions wherein the active ingredients are contained in an amount effective to achieve the intended purpose. More specifically, a therapeutically effective amount means an amount of active ingredients (antibody) effective to prevent, alleviate or ameliorate symptoms of a disorder (e.g., tuberculosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide antibody levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Experimental models are well known in the art.

Passive transfer of serum studies in mouse models have been used to broadly assess the effects of anti-mycobacterial antibodies (Lyashchenko K., Colangeli R., Houde M., Al Jandali H., Menzies D., Gennaro M. L. Heterogeneous antibody responses in tuberculosis. Infect Immun. 1998; 66:3936-3940).

The antibodies are administered to a human subject, in accord with known methods, such as intravenous adminis- tration, for example, as a bolus or by continuous infusion over a period of time, by intramuscular, intraperitoneal, intracerobrospinal, subcutaneous, intra-articular, intrasyn- ovial, intrathecal, oral, topical, or inhalation routes. The antibodies can be administered parenterally, when possible, at the target cell site, or intravenously. In some embodi- ments, antibody is administered by intravenous or subcuta- neous administration. Therapeutic compositions of the invention may be administered to a subject or subject systemically, parenterally, or locally. The above parameters for assessing successful treatment and improvement in the disease are readily measurable by routine procedures famil- iar to a physician.

For parenteral administration, the antibody may be for- mulated in a unit dosage injectable form (solution, suspen- sion, emulsion) in association with a pharmaceutically acceptable, parenteral vehicle. Examples of such vehicles include, but are not limited, water, saline, Ringer's solution, dextrose solution, and 5% human serum albumin. Non- aqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives.

The antibody of some embodiments of the present inven- tion may be administered to the host in any manner, strategy and/or combination available in the art in amounts sufficient to offer a therapeutic treatment against infection by a viru- lent strain of *Mycobacterium tuberculsosis*. These compo- sitions may be provided to the individual by a variety of routes known in the art, especially parenteral routes, includ- ing but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e., administration of the antibody at staggered times by maintaining the sterile condition of the formulation through the treatment regime).

The dose and dosage regimen depends upon a variety of factors readily determined by a physician, such as the nature of the infection, for example, its therapeutic index, the subject, and the subject's history. The progress of this therapy is readily monitored by conventional methods and assays and based on criteria known to the physician or other persons of skill in the art. The above parameters for assess- ing successful treatment and improvement in the disease are readily measurable by routine procedures familiar to a physician.

These antibodies may also be administered via genetic vectors that express the paired heavy and light chains of a given antibody. This can involve a plasmid the efficiently expresses these genes or a viral vector, such as Adenoviral or Adeno-associated virus (AAV) vectors. These vectors can be delivered by injection into muscle tissue, and, depending on the dose, can secrete relatively large amount of secreted antibody into the circulation over a relatively long period of time.

A combined treatment is also envisaged herein for thera- peutic or prophylactic objects, with a pharmaceutical com- pound, such as, but not limited to, antibiotics. Antibiotics that are suitable for co-administration with the antibody of some embodiments of the present invention include, but are not limited to, isoniazid, rifampin, rifapentine, ethambutol, pyrazinamide, bedaquiline, capreomycin, cycloserine, dex- amethasone, kanamycin, and tinocordin. The combined administration includes co-administration, using separate formulations or a single pharmaceutical formulation, and consecutive administration in either order, wherein prefer- ably there is a time period while both (or all) active agents simultaneously exert their biological activities. Such com- bined therapy can result in a synergistic therapeutic effect. The above parameters for assessing successful treatment and improvement in the disease are readily measurable by rou- tine procedures familiar to a physician.

According to another embodiment, the present invention provides a passive vaccine including the antibody of some embodiments (or a polynucleotide encoding the same) of the invention combined with an excipient. Thus, the vaccine comprises other substances (termed excipients) that are present because they improve the immune response (an adjuvant), are necessary for ensuring stability of the product (stabilizers and preservatives), are the vehicle for delivering vaccine (carrier) or are a residual of the manufacturing process (for example antibiotics or cell culture components).

The antibody provided by the present invention may be used to passively immunize individuals against tuberculosis. The protective antibodies produced may be isolated and used as a therapeutic antibody in a manner analogous to the current use of immune or hyperimmune globulin prepara- tions. The immune or hyperimmune globulin may then be passively administered to a subject in need of such protec- tive antibodies.

The high affinity of the antibody of some embodiments or the invention or even more so the fact that it is a human antibody devoid of toxicity renders it particularly suitable for diagnostic (especially in in vivo diagnosis in which the human character of the antibodies is critical) applications.

Thus, according to an aspect of the invention there is provided a method of detecting a *Mycobacterium tubercu- losis* (TB) infection, the method comprising contacting a biological sample suspected of being infected with TB with a human antibody comprising an antigen binding domain which binds PstS1 of *Mycobacterium tuberculosis* (TB) at a $K_D<1$ nM under conditions which allow a specific immu- nocomplex formation between the antibody and the PstS1, wherein a presence of the immunocomplex is indicative of *Mycobacterium tuberculosis* (TB) infection.

According to some embodiments of the invention, con- tacting is effected in-vivo.

According to some embodiments of the invention, con- tacting is effected ex-vivo.

Alternatively or additionally there is provided a diagnos- tic kit for detecting a *Mycobacterium tuberculosis* (TB) infection, the kit comprising a human antibody comprising an antigen binding domain which binds PstS1 of *Mycobac- terium tuberculosis* (TB) at a $K_D<1$ nM under conditions which allow a specific immunocomplex formation between said antibody and the PstS1.

According to a specific embodiment, the antibody is labeled with a detectable moiety.

Once diagnosis is confirmed the subject may be treated with an anti TB drug (e.g., Gold standard) or the antibody or some embodiments of the invention.

The term "detecting", as used herein, refers to the act of detecting, perceiving, uncovering, exposing, visualizing or identifying a PstS1 in the biological sample (in vitro or ex vivo) or in the subject (in vivo diagnosis). The precise method of detecting is dependent on the detectable moiety (also referred to herein as identifiable moiety) to which the antibody is attached as further described herein.

As used herein the term "diagnosing" refers to classifying a disease, determining a severity of a disease (grade or stage), monitoring progression, forecasting an outcome of the disease and/or prospects of recovery.

The subject may be a healthy subject (e.g., human) undergoing a routine well-being checkup. Alternatively, the subject may be at risk of the disease. Yet alternatively, the method may be used to monitor treatment efficacy.

The antibody may comprise e.g., attached to an identifiable moiety. Alternatively or additionally, the antibody may be identified indirectly such as by using a secondary antibody.

As mentioned, the method of the present invention is effected under conditions sufficient to form an immunocomplex (e.g. a complex between the antibodies of the present invention and the PstS1); such conditions (e.g., appropriate concentrations, buffers, temperatures, reaction times) as well as methods to optimize such conditions are known to those skilled in the art, and examples are disclosed herein.

Compositions of some embodiments of the invention may, if desired, be presented in a pack or dispenser device, such as an FDA approved kit (diagnostic or therapeutic), which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Antibody Isolation

To isolate the antibodies that account for this subject's serologic activity, single B cells were sorted using recombinant PstS1 fused to maptose binding protein produced in our laboratory in *E. coli*. A total of 108 heavy chains were isolated, of which 16 antibodies formed 5 different clones (FIG. 1C). Antibody P4-36 is a member of clone 3 showed MTB inhibiting activity.

Protein Production and Purification for Structural Studies

6×-His-tagged PstS1 was expressed in *E. Coli* fused to maltose binding protein and purified from bacteria supernatants using Ni2+-NTA affinity chromatography (GE Healthcare) and Superdex 200 16/60 size exclusion chromatography (SEC) (GE Healthcare).

B Cell Sorting and Antibody Isolation

Single-cell sorting of bait$^+$CD19$^+$IgG$^+$ B cells from patient 004 PBMCs was conducted as previously described [Freund et al A New Glycan-Dependent CD4-Binding Site Neutralizing Antibody Exerts Pressure on HIV-1 In Vivo, PloS pathogens, 2015], [Freund et al, Coexistence of potent HIV-1 broadly neutralizing antibodies and antibody-sensitive viruses in a viremic controller, Science Trans Med, 9, 373, 2017], [Freund et al Amplification of highly mutated human Ig lambda light chains from an HIV-1 infected patient, J Immunol Methods, 418, 61-65, 2015]. Memory B cells were pre-enriched with anti-CD19 magnetic beads (MACS) and stained with PstS1. Rescue primers were used to amplify both heavy chains [Scheid et al Sequence and structural convergence of broad and potent HIV antibodies that mimic CD4 binding, Science, 2011], and Igλ genes [Freund et al Amplification of highly mutated human Ig lambda light chains from an HIV-1 infected patient, J Immunol Methods, 418, 61-65, 2015], and regular primers were used for IgK chain [Scheid et al Sequence and structural convergence of broad and potent HIV antibodies that mimic CD4 binding, Science, 2011]. All PCR products were sequenced and analyzed for Ig gene usage, CDR3, and the number of $V_H/V_L$ somatic hypermutations (IgBLAST, www(dot)ncbi(dot)nlm(dot)nih(dot)gov/igblast; and IMGT, www(dot)imgt(dot)org). Purified, digested PCR products were cloned into human Igγ1-, IgK or Igλ-expression vectors as previously described [Freund et al, Coexistence of potent HIV-1 broadly neutralizing antibodies and antibody-sensitive viruses in a viremic controller, Science Trans Med, 9, 373, 2017] and produced by transient transfection of IgH, IgK and IgL expression plasmids into exponentially growing HEK 293-6E cells as previously described [Freund et al, Coexistence of potent HIV-1 broadly neutralizing antibodies and antibody-sensitive viruses in a viremic controller, Science Trans Med, 9, 373, 2017].

ELISAs

High-binding 96-well ELISA plates (Costar) were coated overnight with 5 μg/mL of purified PstS1 in PBS. After washing 6 times with PBS+0.05% Tween 20, the plates were blocked for 2 h with 2% BSA, 1 μM EDTA and 0.05% Tween-PBS ("blocking buffer"), and then incubated for 1 h with IgGs that were added as seven consecutive 1:4 dilutions in PBS from an initial concentration of 4 μg/mL. After additional washing, the plates were developed by incubation with goat HRP-conjugated anti-human IgG antibodies (Jackson ImmunoResearch) (at 0.8 m/mL in blocking buffer) for 1 h followed by HRP chromogenic substrate (ABTS solution; Invitrogen). All experiments were performed at least 3 times.

For competition ELISAs, the plates were coated with 2 μg/mL purified PstS1 in PBS. washed, blocked for 2 h with blocking buffer and then incubated for 1 h with IgGs added as seven consecutive 1:4 dilutions in PBS from an initial concentration of 32 μg/mL, and in the presence of biotinylated antibody at a constant concentration of 4 μg/mL. The plates were then incubated for 1 h with HRP-conjugated streptavidin (Jackson ImmunoResearch) at 1 μg/mL in blocking buffer, followed by HRP chromogenic substrate (ABTS solution; Invitrogen). All experiments were performed at least 3 times.

Statistical Analyses

Statistical differences were analyzed by the Mann-Whitney test. GraphPad Prism software was used for analysis, and data were considered significant at *$p \leq 0.05$, $p \leq 0.01$, and *$p \leq 0.001$.

Example 1

Isolation of Anti Tb Antibodies from Human Patients

Twenty six actively infected patients from the Israeli Lung Department, Shmuel Harofe Hospital, Israel, were recruited for this study. All patients were hospitalized due to active Tb disease and received treatment with antibiotics. With the aim of isolating antibodies developed in Mtb-infected patients during active Mtb infection, the present inventors focused on antibody responses directed towards protein components of Mtb. Mtb genome has over 3900 open reading frames (ORFs) encoding thousands of different proteins. However, since antibodies are in the extracellular milieu, they usually are directed against proteins that are located at the bacterial surface. Several proteins were previously reported to elicit antibodies responses in Mtb-infected patients. The present inventors isolated six proteins that were previously reported to be recognized by sera from Mtb infected individuals, that are unique to Mtb and finally, which are known virulence factors of the bacteria—Ag85b, CFP10-ESAT6 complex, Hbha, Malate Synthase and PstS1. These proteins were expressed and affinity purified and used as probes to screen patient sera in ELISA (FIG. 1A).

The strongest responses detected were against the PstS1 protein—16 out of the 26 patients tested responded and 6 patients responded strongly (patients 2, 4, 6, 9, 15 and 22, FIGS. 1A and F). For the other antigens—16 patients responded to Ag85b, of which 4 responded strongly (FIGS. 1B, and F), 14 responded to CFP10-ESAT6 complex, of which one patient 29 responded strongly (FIGS. 1C and F). Weaker responses were observed against Hbha and MS (FIGS. 1D, E and F). Overall, 5 patients (p.2, p.4, p.9, p.22 and p.28) responded to all five antigens and 21 patients responded to at least one antigen in the panel (FIG. 1F).

Anti-Mtb antibody responses were also tested by testing serum reactivity to bacterial lysate from the attenuated strain H37Ra (FIG. 1G). As can be seen, the actively infected patients in the present Mtb-infected cohort of patients have antibody responses against inactivated bacterial lysate as well as against recombinant Mtb proteins.

Example 2

Characterization of the Anti Tb Antibodies

To characterize the anti-Mtb antibodies developed in patients during active infection on a monoclonal level, the present inventors focused on one patient from the cohort, Patient 109004, which was nominated P.4, who had exceptionally high serum response to PstS1 (FIG. 1A). For this, 150 ml of whole blood were collected from the donor followed by PBMC isolation. A total of 150 million cells were obtained and these cells were subjected to B cell enrichment using CD20 magnetic beads. Using flow cytometry single PstS1-positive were sorted, IgG positing B cells, which comprised 0.5% of the entire B cell population (FIG. 2A). These cells were subjected to RT and PCR similarly to what was previously described [Freund et al, Coexistence of potent HIV-1 broadly neutralizing antibodies and antibody-sensitive viruses in a viremic controller, Science Trans Med, 9, 373, 2017]. A total of 108 heavy chains were amplified and a total of 96 light chains. In response to an infection, pathogen-specific B cells undergo clonal expansion. therefore, the antibodies were tested for clonality as was previously described [Freund et al, Coexistence of potent HIV-1 broadly neutralizing antibodies and antibody-sensitive viruses in a viremic controller, Science Trans Med, 9, 373, 2017]. Shortly, each antibody sequence was aligned to IgBlast database and the closest VH, DH, JH, VL and JL gene segments were identified. Clonally related antibodies were identified if two or more different antibodies were encoded by the same germline VH, DH, JH, VL and JL gene segments. Additional requirement for clonality was similarity of amino acid sequence of at least 75% in the amino acid sequence of CDRH3 of antibodies coming from different cells. It was found that 14.8% of the antibodies were clonally related (FIG. 1C) and comprised a total of five clones (Table 2).

TABLE 2

| complete amino acid sequences and CDR sequences (Kabat) of antibodies of some embodiments of the invention | | | |
|---|---|---|---|
| Clone | Name | SEQ ID NO: | Sequence |
| 1 | P4-110 IgH | 1 | EVQLVQSGGGLVKPGGSLRLSCAASGFTFSRHTMHWVRLAPGK GLEWVSSILSSPTYIYYADSVKGRFTISRDNSGNSLFLQMNSLRVD DTAVYYCARGDYYYDGVASDPHFDNWGQGTLVTVSS |
| 1 | CDRH1 | 2 | GFTFSRHT |
| 1 | CDRH2 | 3 | ILSSPTYI |
| 1 | CDRH3 | 4 | ARGDYYYDGVASDPHFDN |
| 1 | P4-110 IgL | 5 | QSVLTQTPSASGTPGQRVTISCSGSRSNIGSNYVYWFQQFPGAAP QLLISRNIQRPSGVPARFSGSKSDTSASLAISGLRSEDEAHYYCAA WDDSLSGVVFGGGTKVTVL |
| 1 | CDRL1 | 6 | RSNIGSNY |
| 1 | CDRL2 | 7 | RNI |

TABLE 2-continued

| | | complete amino acid sequences and CDR sequences (Kabat) of antibodies of some embodiments of the invention | |
|---|---|---|---|
| Clone | Name | SEQ ID NO: | Sequence |
| 1 | CDRL3 | 8 | AAWDDSLSGVV |
| 1 | P4-143 IgH | 9 | EVQLVESGGGLVKPGGSLRLSCAASGFTFESHRMHWVRQAPGK GLEWVSSIISSRTYIYYADSVKGRFTISRDNSRNSLFLQMNSLRAE DTAVYYCARGDYYYDGVASDPHFDNWGQGTLVTVSS |
| 1 | CDRH1 | 10 | GFTFESHR |
| 1 | CDRH2 | 11 | IISSRTYI |
| 1 | CDRH3 | 12 | ARGDYYYDGVASDPHFDN |
| 1 | P4-143 IgL | 13 | SNYVYWFQQLPGTAPQLLIYRNIQRPSGVPARFSGSKSGTSASLAI SGLRSEDEADYYCATWDDSLSGVVFGGGTKVTVL |
| 1 | CDRL1 | 14 | SNIGSNY |
| 1 | CDRL2 | 15 | RNI |
| 1 | CDRL3 | 16 | ATWDDSLSGVV |
| 1 | P4-163 IgH | 17 | EVQLVESGGGLVKPGGSLRLSCAASGFTFESHRMHWVRQAPGK GLEWVSSIISSRTYIYYADSVKGRFTISRDNSRNSLFLQMNSLRAE DTAVYYCARGDYYYDGVASDPHFDNWGQGTLVTVSS |
| 1 | CDRH1 | 18 | GFTFESHR |
| 1 | CDRH2 | 19 | IISSRTYI |
| 1 | CDRH3 | 20 | ARGDYYYDGVASDPHFDN |
| 1 | P4-163 IgL | 21 | QSVLTQPPSASGTPGQRVTISCSGGRSNIGSNYVYWFQQLPGTAP QLLIYRNIQRPSGVPARFSGSKSGTSASLAISGLRSEDEADYYCAT WDDSLSGVVFGGGTKVTVL |
| 1 | CDRL1 | 22 | RSNIGSNY |
| 1 | CDRL2 | 23 | RNI |
| 1 | CDRL3 | 24 | ATWDDSLSGVV |
| 1 | P4-123 IgH | 25 | EVQLVESGGGLVKPGGSLRLSCAASGFTFESHRMHWVRQAPGK GLEWVSSIISSRTYIYYADSVKGRFTISRDNSRNSLFLQMNSLRAE DTAVYYCARGDYYYDGVASDPHFDNWGQGTLVTVSS |
| 1 | CDRH1 | 26 | GFTFESHR |
| 1 | CDRH2 | 27 | IISSRTYI |
| 1 | CDRH3 | 28 | ARGDYYYDGVASDPHFDN |
| 1 | P4-123 IgL | 29 | QSVLTQPPSASGTPGQRVTISCSGGRSNIGSNYVYWFQQLPGTAP QLLIYRNIQRPSGVPARFSGSKSGTSASLAISGLRSEDEADYYCAT WDDSLSGVVFGGGTKVTVL |
| 1 | CDRL1 | 30 | RSNIGSNY |
| 1 | CDRL2 | 31 | RNI |
| 1 | CDRL3 | 32 | ATWDDSLSGVV |
| 1 | P4-170 IgH | 33 | EVQLVESGGGLVKPGGSLRLSCAASGFTFSSHRMHWVRQAPGK GLEWVSSIISSRTYIYYADSVKGRFTISRDNSGNSLFLQMNSLRVE DTAVYYCARGDYYYDGVASDPHFDNWGQGTLVTVSS |
| 1 | CDRH1 | 34 | GFTFSSHR |
| 1 | CDRH2 | 35 | IISSRTYI |
| 1 | CDRH3 | 36 | ARGDYYYDGVASDPHFDN |

TABLE 2-continued

| | | | |
|---|---|---|---|
| complete amino acid sequences and CDR sequences (Kabat) of antibodies of some embodiments of the invention | | | |

| Clone | Name | SEQ ID NO: | Sequence |
|---|---|---|---|
| 1 | P4-170 IgL | 37 | QSVLTQTPSASGTPGQRVTISCSGSRSNIGSNYVYWFQQFPGAAP QLLIYRNIQRPSGVPARFSGSKSDTSASLAISGLRSEDEAHYYCAA WDDSLSGVVFGGGTKVTVL |
| 1 | CDRL1 | 38 | RSNIGSNY |
| 1 | CDRL2 | 39 | RNI |
| 1 | CDRL3 | 40 | AAWDDSLSGVV |
| 1 | P4-66 IgH | 41 | EVQLVESGGGLVKPGGSLRLSCAASGFTFSSHRMHWVRQAPGK GLEWVSSIISSRTYIYYADSVKGRFTISRDNSGNSLFLQMNSLRVE DTAVYYCARGDYYYDGVASDPHFDNWGQGTLVTVSS |
| 1 | CDRH1 | 42 | GFTFSSHR |
| 1 | CDRH2 | 43 | IISSRTYI |
| 1 | CDRH3 | 44 | ARGDYYYDGVASDPHFDN |
| 1 | P4-66 IgL | 45 | QSVLTQTPSASGTPGQRVTISCSGSRSNIGSNYVYWFQQFPGAAP QLLIYRNIQRPSGVPARFSGSKSDTSASLAISGLRSEDEAHYYCAA WDDSLSGVVFGGGTKVTVL |
| 1 | CDRL1 | 46 | RSNIGS |
| 1 | CDRL2 | 47 | RNI |
| 1 | CDRL3 | 48 | AAWDDSLSGVV |
| 1 | P4-9 IgH | 49 | EVQLVESGGGLVKPGGSLRLSCAASGFTFSSHRMHWVRQAPGK GLEWVSSIISSRTYIYYADSVKGRFTISRDDSRNSLFLQMNSLRAE DTAVYYCARGDYYYDGVASDPHFDNWGQGTLVTVSS |
| 1 | CDRH1 | 50 | GFTFSSHR |
| 1 | CDRH2 | 51 | IISSRTYI |
| 1 | CDRH3 | 52 | ARGDYYYDGVASDPHFDN |
| 1 | P4-9 IgL | 53 | QSVLTQPPSASGTPGQRVTISCSGSRSNIGSNYVYWFQQLPGTAP QLLIYRNIQRPSGVPARFSGSKSGTSASLAISGLRSEDEADYYCAA WDDSLSGVVFGGGTKVTVL |
| 1 | CDRL1 | 54 | RSNIGSNY |
| 1 | CDRL2 | 55 | RNI |
| 1 | CDRL3 | 56 | AAWDDSLSGVV |
| 2 | P4-141 IgH | 57 | EVQLVESGGGLVQPGGSLRLSCAASTFTFNSYWMHWVRQAPGK GLVWVSLINPDGSTTKSADSVKGRFTISRDNAENTLYLQMNSLR AEDTAIYYCAGAYSSGWYKRWGQGTLVTVSS |
| 2 | CDRH1 | 58 | TFTFNSYW |
| 2 | CDRH2 | 59 | INPDGSTT |
| 2 | CDRH3 | 60 | AGAYSSGWYKR |
| 2 | P4-141 IgL | 61 | DIQMTQSPSSLSASVGDRVTISCRASQGISRSLAWYQQKPGKAPQ LLLYGASRLESGVPSRFSGTGSGTDYTLTISSLQPEDFATYYCQQY YNVPYTFGQGTKLEIK |
| 2 | CDRL1 | 62 | QGISRS |
| 2 | CDRL2 | 63 | GAS |
| 2 | CDRL3 | 64 | QQYYNVPYT |
| 2 | P4-48 IgH | 65 | EVQLVQSGGGLVQPGGSLRLSCAASTFTFSSYWMHWVRQAPGK GLVWVSLINPDGSTTKSADSVKGRFTISRDNAENTLYLQMNSLR ADDTAIYYCAGAYSSGWYKRWGQGTLVAVSS |

TABLE 2-continued complete amino acid sequences and CDR sequences (Kabat) of
antibodies of some embodiments of the invention

| Clone | Name | SEQ ID NO: | Sequence |
|---|---|---|---|
| 2 | CDRH1 | 66 | TFTFSSYW |
| 2 | CDRH2 | 67 | INPDGSTT |
| 2 | CDRH3 | 68 | AGAYSSGWYKR |
| 2 | P4-85 IgH | 69 | EVQLVQSGGGLVQPGGSLRLSCAASTFTFSSYWMHWVRQAPGK<br>GLVWVSLINPDGSTTKSADSVKGRFTISRDNAENTLYLQMNSLR<br>AEDTAIYYCAGAYSSGWYKRWGQGTLVAVSS |
| 2 | CDRH1 | 70 | INPDGSTT |
| 2 | CDRH2 | 71 | TFTFSSYW |
| 2 | CDRH3 | 72 | AGAYSSGWYKR |
| 3 | P4-107 IgH | 73 | EVQLVESGGGLVQPGRSLRLSCTDSGFTFSEYALSWVRQAPGKG<br>LEWVGFIRSKAYGGTTEYAASVKGRFTISRDDSKSVAYLQMNSL<br>KTEDTAVYFCTGPRPYYDSSGYYPYYFDYWGQGTLVTVSS |
| 3 | CDRH1 | 74 | GFTFSEYA |
| 3 | CDRH2 | 75 | IRSKAYGGTT |
| 3 | CDRH3 | 76 | TGPRPYYDSSGYYPYYFDY |
| 3 | P4-107 IgL | 77 | QSALTQPRSVSGSPGQSVTISCTGSRSDVGGYDYVSWYQQHPGR<br>VPKLMIYDVTKRPSGVPDRFSGSRSGNTASLTISGLQADDEADYY<br>CSSFAGSSTYVVFGGGTTLTVL |
| 3 | CDRL1 | 78 | RSDVGGYDY |
| 3 | CDRL2 | 79 | DVT |
| 3 | CDRL3 | 80 | SSFAGSSTYVV |
| 3 | P4-36 IgH | 81 | EVQLVESGGGLVQPGRSLRLSCTDSGFTFSEYALSWVRQAPGKG<br>LEWVGFIRSKAYGGTTEYAASVKGRFTISRDDSKSVAYLQMNSL<br>KTEDTAVYFCTGPRPYYDSSGYYPYYFDYWGQGTLVTVSS |
| 3 | CDRH1 | 82 | GFTFSEYA |
| 3 | CDRH2 | 83 | IRSKAYGGTT |
| 3 | CDRH3 | 84 | TGPRPYYDSSGYYPYYFDY |
| 3 | P4-36 IgL | 85 | QSALTQPRSVSGSPGQSVTISCTGSRSDVGGYDYVSWYQQHPGR<br>VPKLMIYDVTKRPSGVPDRFSGSRSGNTASLTISGLQADDEADYY<br>CSSFAGSSTYVVFGGGTTLTVL |
| 3 | CDRL1 | 86 | RSDVGGYDY |
| 3 | CDRL2 | 87 | DVT |
| 3 | CDRL3 | 88 | SSFAGSSTYVV |
| 4 | P4-31 IgH | 89 | QVQLVQSGAEVKNPGASVKIACVASGHNFSDFYFHWVRQAPGQ<br>GLEWMGIVKGGGGVTGYPQRLKGRVTMTTDTSTRTIYLELKNLT<br>SDDTATYYCARDPGCNGGSCYYFDHWGRGTLVT |
| 4 | CDRH1 | 90 | GHNFSDFY |
| 4 | CDRH2 | 91 | VKGGGGVT |
| 4 | CDRH3 | 92 | ARDPGCNGGSCYYFDH |
| 4 | P4-31 IgL | 93 | SYELTQSTSMSVSPGQTATITCSGDALPKQYAYWYQQKSGQAPT<br>LLIYKDNQRSSGIPDRFSGSSSGTTLTLTISGVQTEDEAVYHCQSS<br>DITSRFVIFGGGTKLTVL |
| 4 | CDRL1 | 94 | ALPKQY |

TABLE 2-continued complete amino acid sequences and CDR sequences (Kabat) of
antibodies of some embodiments of the invention

| Clone | Name | SEQ ID NO: | Sequence |
|---|---|---|---|
| 4 | CDRL2 | 95 | KDN |
| 4 | CDRL3 | 96 | QSSDITSRFVI |
| 4 | P4-62 IgH | 97 | VQLVQSGAEVKKPGASLRLACTASGYNFSDFYIHWVRQAPGQG LEWMGIVKGGGGVTGYPQALRSRVTMTTDTSTTTVYMELKNISS EDTAIYYCARDPGCNGGSCYYFDHWGRGTLVTVSS |
| 4 | CDRH1 | 98 | GYNFSDFY |
| 4 | CDRH2 | 99 | VKGGGGVT |
| 4 | CDRH3 | 100 | ARDPGCNGGSCYYFDH |
| 5 | P4-13 IgH | 101 | VQLVQSGGGLVKPGGSLRLSCAASGFTFSDYYMSWIRQAPGKGL EWVSYISSSGGTVYYADSVKGRFTISRDNANNALYLQMNSLRAE DTAVYFCARDLDSASWSGYYYYYSMYVWGQGTTVTVSS |
| 5 | CDRH1 | 102 | GFTFSDYY |
| 5 | CDRH2 | 103 | ISSSGGTV |
| 5 | CDRH3 | 104 | ARDLDSASWSGYYYYYSMYV |
| 5 | P4-67 IgH | 105 | VQLVQSGGGLVKPGGSLRLSCAASGFTFSDYYMSWIRQAPGKGQ EWVSYISSSGGTVYYADSGKGRFTISRDNANNGQYQQMNSERAE DTAVYFCARDVDSASWSGYYYYYSMYVWGQGTTVTVSS |
| 5 | CDRH1 | 106 | GFTFSDYY |
| 5 | CDRH2 | 107 | ISSSGGTV |
| 5 | CDRH3 | 108 | ARDVDSASWSGYYYYYSMYV |

TABLE 3

Summary of the antibodies

| Clone | Antibody | Closest VH | Closest VL | Somatic Mutations in V (nt) % VH | VL | CDRH3 Sequence | CDRH3 Length |
|---|---|---|---|---|---|---|---|
| 1 | P4-110 | 3-21 | L1-47 | 9.26 | 6.13 | ARGDYYYDGVASDPHFDN (SEQ ID NO: 4) | 18 |
| 1 | P4-143 | 3-21 | L1-47 | 7.27 | 3.5 | ARGDYYYDGVASDPHFDN (SEQ ID NO: 12) | 18 |
| 1 | P4-163 | 3-21 | L1-47 | 7.27 | 3.5 | ARGDYYYDGVASDPHFDN (SEQ ID NO: 20) | 18 |
| 1 | P4-123 | 3-21 | L1-47 | 7.27 | 3.9 | ARGDYYYDGVASDPHFDN (SEQ ID NO: 28) | 18 |
| 1 | P4-170 | 3-21 | L1-47 | 6.88 | 5.75 | ARGDYYYDGVASDPHFDN (SEQ ID NO: 36) | 18 |
| 1 | P4-66 | 3-21 | L1-47 | 6.88 | 5.37 | ARGDYYYDGVASDPHFDN (SEQ ID NO: 44) | 18 |
| 1 | P4-9 | 3-21 | L1-47 | 5.7 | 3.52 | ARGDYYYDGVASDPHFDN (SEQ ID NO: 52) | 19 |
| 2 | P4-141 | 3-74 | K1-NL1 | 8.05 | 3.35 | AGAYSSGWYKR (SEQ ID NO: 60) | 11 |

TABLE 3-continued

Summary of the antibodies

| Clone | Antibody | Closest VH | Closest VL | Somatic Mutations in V (nt) % VH | VL | CDRH3 Sequence | CDRH3 Length |
|---|---|---|---|---|---|---|---|
| 2 | P4-48 | 3-74 | | 9.25 | | AGAYSSGWYKR (SEQ ID NO: 68) | 11 |
| 2 | P4-85 | 3-74 | | 8.05 | | AGAYSSGWYKR (SEQ ID NO: 60) | 11 |
| 3 | P4-107 | 3-49 | L2-11 | 3.84 | 4.99 | TGPRPYYDSSGYYPYYFDY (SEQ ID NO: 76) | 19 |
| 3 | P4-36 | 3-49 | L2-11 | 4.2 | 4.9 | TGPRPYYDSSGYYPYYFDY (SEQ ID NO: 84) | 19 |
| 4 | P4-31 | 1-46 | L3-25 | 23.3 | 12.8 | ARDPGCNGGSCYYFDH (SEQ ID NO: 92) | 16 |
| 4 | P4-62 | 1-46 | | 21.4 | | ARDPGCNGGSCYYFDH (SEQ ID NO: 100) | 16 |
| 5 | P4-13 | 3-11 | | 4.24 | | ARDLDSASWSGYYYYYSMYV (SEQ ID NO: 104) | 20 |
| 5 | P4-67 | 3-11 | | 7.27 | | ARDVDSASWSGYYYYYSMYV (SEQ ID NO: 108) | 20 |

Five antibodies were expressed: From clone 1: P4-163 (SEQ IDs 17-24), P4-170 (SEQ IDs 33-40), from clone 2: P4-141 (SEQ IDs 57-64), from clone 3: P4-36 (SEQ ID 81-88), from clone 4: P4-31 (SEQ ID 89-96). All the antibodies were cloned into IgH and IgK or IgL expression vectors and used for transfection of 293Epi cells as described before [Freund et al, Coexistence of potent HIV-1 broadly neutralizing antibodies and antibody-sensitive viruses in a viremic controller, Science Trans Med, 9, 373, 2017].

All the expressed mAbs bound strongly to PstS1, which is the cognate target of the antibodies in ELISA (FIG. 3A). Antibodies P4-31 and P4-163, as well as P4-170 had a certain amount of cross reactivity to MBP, which indicates that they are less specific to PstS1 and have some amount of binding to the carrier protein (FIG. 3B). Antibody P4-36 was specific to PstS1 and did not show any binding to MBP. In staining of the whole live pathogenic Mtb bacteria TB Erdman only antibody P4-36 showed robust staining that was located to the plasma bacterial surface (FIG. 3C). It is therefore concluded that antibody P4-36 isolated from an infected patient binds specifically to PstS1 on the surface of Mtb bacteria and therefore represents the first an anti-Mtb monoclonal antibody directed against this target.

Next, the ability of anti-PstS1 antibodies to inhibit Mtb pathogenesis in host cells was tested. First the effect of P4-36 on bacterial uptake by macrophages was tested. For this, two strains of bacteria were used: the pathogenic TB Erdman strain and the attenuated H37Ra strain. An increase in the number of bacteria that entered the cells when P4-36 antibody was added was evident (FIG. 4).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of preventing or treating *Mycobacterium tuberculosis* (TB) in a subject in need thereof, the method comprising administering to the subject an effective amount of an antibody capable of binding Psts1 of TB, wherein said antibody is selected from the group consisting of:

(i) an antibody comprising CDRH1 comprising SEQ ID NO: 2, CDRH2 comprising SEQ ID NO: 3, CDRH3 comprising SEQ ID NO: 4, CDRL1 comprising SEQ ID NO: 6, CDRL2 comprising SEQ ID NO: 7 and CDRL3 comprising SEQ ID NO: 8;

(ii) an antibody comprising CDRH1 comprising SEQ ID NO: 10, CDRH2 comprising SEQ ID NO: 11, CDRH3 comprising SEQ ID NO: 12, CDRL1 comprising SEQ ID NO: 14, CDRL2 comprising SEQ ID NO: 15 and CDRL3 comprising SEQ ID NO: 16;

(iii) an antibody comprising CDRH1 comprising SEQ ID NO: 18, CDRH2 comprising SEQ ID NO: 19, CDRH3 comprising SEQ ID NO: 20, CDRL1 comprising SEQ ID NO: 22, CDRL2 comprising SEQ ID NO: 23 and CDRL3 comprising SEQ ID NO: 24;

(iv) an antibody comprising CDRH1 comprising SEQ ID NO: 26, CDRH2 comprising SEQ ID NO: 27, CDRH3 comprising SEQ ID NO: 28, CDRL1 comprising SEQ ID NO: 30, CDRL2 comprising SEQ ID NO: 31 and CDRL3 comprising SEQ ID NO: 32;

(v) an antibody comprising CDRH1 comprising SEQ ID NO: 34, CDRH2 comprising SEQ ID NO: 35, CDRH3 comprising SEQ ID NO: 36, CDRL1 comprising SEQ ID NO: 38, CDRL2 comprising SEQ ID NO: 39 and CDRL3 comprising SEQ ID NO: 40;

(vi) an antibody comprising CDRH1 comprising SEQ ID NO: 42, CDRH2 comprising SEQ ID NO: 43, CDRH3 comprising SEQ ID NO: 44, CDRL1 comprising SEQ ID NO: 46, CDRL2 comprising SEQ ID NO: 47 and CDRL3 comprising SEQ ID NO: 48;

(vii) an antibody comprising CDRH1 comprising SEQ ID NO: 50, CDRH2 comprising SEQ ID NO: 51, CDRH3 comprising SEQ ID NO: 52, CDRL1 comprising SEQ ID NO: 54, CDRL2 comprising SEQ ID NO: 55 and CDRL3 comprising SEQ ID NO: 56; and viii) an antibody comprising CDRH1 comprising SEQ ID NO: 58, CDRH2 comprising SEQ ID NO: 59, CDRH3 comprising SEQ ID NO: 60, CDRL1 comprising SEQ ID NO: 62, CDRL2 comprising SEQ ID NO: 63 and CDRL3 comprising SEQ ID NO: 64, wherein said CDRH1, CDRH2, CDRH3 are arranged from N to C on the heavy chain of said antibody and CDRL1, CDRL2 and CDRL3 are arranged from N to C on the light chain of said antibody, thereby preventing or treating TB in the subject.

*    *    *    *    *